United States Patent
Heidmann

(10) Patent No.: US 9,779,769 B2
(45) Date of Patent: *Oct. 3, 2017

(54) INTEGRATED OPTICAL NANOSCALE PROBE

(71) Applicant: Infinitum Solutions, Inc., Santa Clara, CA (US)

(72) Inventor: Juergen Heidmann, Salinas, CA (US)

(73) Assignee: Infinitum Solutions, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/952,852

(22) Filed: Nov. 25, 2015

(65) Prior Publication Data

US 2016/0077167 A1 Mar. 17, 2016

Related U.S. Application Data

(63) Continuation-in-part of application No. 14/542,410, filed on Nov. 14, 2014, now Pat. No. 9,482,612, and
(Continued)

(51) Int. Cl.
*G01R 33/26* (2006.01)
*G11B 5/455* (2006.01)
(Continued)

(52) U.S. Cl.
CPC ............ *G11B 5/455* (2013.01); *G01N 21/64* (2013.01); *G01N 21/6489* (2013.01);
(Continued)

(58) Field of Classification Search
CPC . G01N 21/6458; G01N 21/6428; G01N 24/00
See application file for complete search history.

(56) References Cited

U.S. PATENT DOCUMENTS 5,770,856 A 6/1998 Fillard et al.
6,259,104 B1 7/2001 Baer
(Continued)

FOREIGN PATENT DOCUMENTS

WO WO 2014/051886 A1 4/2014

OTHER PUBLICATIONS

Challener et al. "Near-field optics for heat-assisted magnetic recording (experiment, theory, and modeling)," *Modelling and Numerical Simulations II*, Modern Aspects of Electrochemistry 44:53-110, 2009.
(Continued)

*Primary Examiner* — Marcus Taningco
(74) *Attorney, Agent, or Firm* — Silicon Valley Patent Group LLP

(57) ABSTRACT

A diamond probe is suitable to be attached to an Atomic Force Microscope and is created with a tip that incorporates a one or more Nitrogen Vacancy (NV) centers located near the end of the tip. The probe arm acts as an optical waveguide to propagate the emission from the NV center with high efficiency and a beveled end directs excitation light to the NV center and directs photoluminescence light emanating from the NV center into the probe arm. The light source (or a portion of the light source), a detector, as well as an RF antenna, if used, may be mounted to the probe arm. The probe with integrated components enable excitation of photoluminescence in the NV center as well as optically detected Electron Spin Resonance (ODMR) and temperature measurements, and may further serve as a light probe utilizing the physical effect of Stimulated Emission Depletion (STED).

39 Claims, 20 Drawing Sheets

Related U.S. Application Data a continuation-in-part of application No. 14/532,992, filed on Nov. 4, 2014, now Pat. No. 9,472,217, which is a continuation-in-part of application No. 14/184,610, filed on Feb. 19, 2014, now Pat. No. 8,885,301.

(60) Provisional application No. 61/950,596, filed on Mar. 10, 2014.

(51) Int. Cl.
| | |
|---|---|
| G01N 21/64 | (2006.01) |
| G11B 5/012 | (2006.01) |
| G01N 24/10 | (2006.01) |
| G01R 33/32 | (2006.01) |
| G11B 5/00 | (2006.01) |

(52) U.S. Cl.
CPC .......... *G01N 24/10* (2013.01); *G01R 33/323* (2013.01); *G11B 5/012* (2013.01); *G01N 2201/0612* (2013.01); *G11B 2005/0021* (2013.01)

(56) References Cited

U.S. PATENT DOCUMENTS

| | | | |
|---|---|---|---|
| 6,389,210 | B1 | 5/2002 | Mukasa et al. |
| 6,891,151 | B2 | 5/2005 | Shimada et al. |
| 7,305,869 | B1 | 12/2007 | Berman et al. |
| 7,861,316 | B2 | 12/2010 | van der Weide et al. |
| 8,193,808 | B2 | 6/2012 | Fu et al. |
| 8,415,640 | B2 | 4/2013 | Babinec et al. |
| 8,455,278 | B2 | 6/2013 | Linares et al. |
| 8,547,090 | B2 | 10/2013 | Lukin et al. |
| 8,885,301 | B1 | 11/2014 | Heidmann |
| 9,472,217 | B2 * | 10/2016 | Heidmann ............ G01N 24/08 |
| 2010/0308813 | A1 | 12/2010 | Lukin et al. |
| 2012/0019242 | A1 | 1/2012 | Hollenberg et al. |
| 2013/0032734 | A1 | 2/2013 | Santori et al. |
| 2014/0166904 | A1 | 6/2014 | Walsworth et al. |
| 2015/0235661 | A1 | 8/2015 | Heidmann |
| 2015/0253355 | A1 | 9/2015 | Grinolds et al. |
| 2016/0282427 | A1 * | 9/2016 | Heidmann ............ G01R 33/26 |

OTHER PUBLICATIONS

Chen et al. "Sub-diffraction optical manipulation of the chargestate of nitrogen vacancy center in diamond", ArXiv e-prints, 21 pages, 2014.

Chernyshov et al. "Measurement of Magnetic Properties Relevant to Heat-Assisted-Magnetic-Recording", *IEEE Transactions on Magnetics* 49(7):3572-3575, 2013.

Chmyrov et al. "Nanoscopy with more than 100,000 'doughnuts'" *Nature Methods* 10(8):737-743, 2013.

Han et al. "Three-Dimensional Stimulated Emission Depletion Microscopy of Nitrogen-Vacancy Centers in Diamond Using Continuous-Wave Light", *Nano Lett* 9(9):3323-3329, 2009.

Hao et al. "Effects of polarization on the de-excitation dark focal spot in STED microscopy," *Journal of Optics* 12(11):115707-1-8, 2010.

Moneron et al. "Two-photon excitation STED microscopy," *Opt Express* 17(17):14567-14573, 2009.

Rittweger et al. "Far-field fluorescence nanoscopy of diamond color centers by ground state depletion," *EPL (Europhysics Letters)* 86(1):14001, 2009.

Rittweger, E. et al. "STED microscopy reveals crystal colour centres with nanometric resolution," *Nature Photonics* DOI:10.1038/NPHOTON.2009.2:1-4, 2009.

Rottmayer et al. "Heat-Assisted Magnetic Recording," *IEEE Trans Magnetics* 42(10):2417-2421, 2006.

Schrof et al. "STED nanoscopy with mass-produced laser diodes," *Optics Express* 19(9): 8066-8072, 2011.

Seigler et al. "Integrated Heat Assisted Magnetic Recording Head: Design and Recording Demonstration," *IEEE Trans Magnetics* 44(1):119-124, 2008.

Vicidomini et al. "STED Nanoscopy with Time-Gated Detection: Theoretical and Experimental Aspects," *Plos One* 8(1):e54421:1-12, 2013.

Wang et al. "Time-gated STED nanoscopy," located at http://www.paper.edu.cn, p. 1-8, 2013.

Willig et al. "STED microscopy with continuous wave beams," *Nat Meth* 4(11):915-918, 2007.

Choy, J. et al. (May 20, 2011). Enhanced Single Photon Emission from a Diamond-Silver Aperture, arXIV:1105.4096v1 [*quant-ph*] p. 1-16.

Doherty, M. et al. (Oct. 28, 2013). "The temperature shifts of the resonances of the NV-center in diamond," arXiv:1310.7303v1 [*cond-mat.mtrl-sci*] p. 1-6.

Epstein, R. et al. (2005). "Anisotropic interactions of a single spin and dark-spin spectroscopy in diamond," Center for Spintronics and Quantum Computation, University of California, Santa Barbara, CA, p. 1-17.

Fuchs, G. et al. (Jun. 11, 2008). "Excited-state spectroscopy using single-spin manipulation in diamond," arXiv:0806.1939v1 [*quant-ph*] p. 1-15.

Greffet, J.-J. et al. (Jul. 3, 2011). "Diamond particles as nanoantennas for nitrogen-vacancy color centers," arXiv:1107.0502v1 [*physics. optics*] p. 1-4.

Grinolds, M. et al. (Sep. 2, 2012). "Nanoscale magnetic imaging of a single electron spin under ambient conditions," arXiv:1209.0203v1 [*cond-mat.mes-hall*] p. 1-12.

Grinolds. (2014). "Nanoscale Magnetic Resonance Imaging and Magnetic Sensing Using Atomic Defects in Diamond," PhD thesis. Harvard University: Cambridge, Massachusetts, 152 pages.

Gruber, A. et al. (1997). "Scanning Confocal Optical Microscopy and Magnetic Resonance on Single Defect Centers," *Science* 276: 2012.

Han, K. et al. (Jul. 22, 2010). "Metastable Dark States Enable Ground State Depletion Microscopy of Nitrogen Vacancy Centers in Diamond with Diffraction-Unlimited Resolution," *Nano Lett* 10: 3199-3203.

Hausmann, B. et al. (Apr. 5, 2011). "Single-color centers implanted in diamond nanostructures," *New Journal of Physics* 13(045004):1-11.

Hong, S. et al. (Feb. 8, 2012). "Coherent, mechanical control of a single electronic spin," arXiv:1202.1823v1 [*cond-mat.mes-hall*] p. 1-6.

Horowitz, V. et al. (Jun. 7, 2012). "Electron spin resonance of nitrogen-vacancy centers in optically trapped nanodiamonds," arXIV:1206.1573v1 [*cond-mat.mtrl-sci*] p. 1-29.

Kucsko, G. et al. (Apr. 3, 2013). "Nanometer scale quantum thermometry in a living cell," arXIV:1304.1068v1 [*quant-ph*] p. 1-22.

Lai, N. et al. (Sep. 8, 2009). "Influence of a static magnetic field on the photoluminescence of an ensemble of Nitrogen-Vacancy color centers in a diamond single-crystal," arXiv:0908.1327v2 [*cond-mat.mtrl-sci*] p. 1-4.

Lai et al. (2013). "Quenching nitrogen-vacancy center photoluminescence with an infrared pulsed laser," New J. Phys.15 033030 <http://iopscience.iop.org/1367-2630/15/3/033030>.

Laraoui, A. et al. (May 7, 2013). "High-Resolution Correlation Spectroscopy of 13C Spins Near a Nitrogen-Vacancy Center in Diamond," arXiv:1305.1536v1 [*cond-mat.mes-hall*] p. 1-22.

Le Sage et al. (2012). "Efficient Photon Detection from Color Centers in a Diamond Optical Waveguide," *Physical Review* B 85:121202-1-4.

Lesik, M. et al. (Jan. 13, 2014). "Perfect preferential orientation of nitrogen-vacancy defects in a synthetic diamond sample," arXiv:1401.2795v1 [*cond-mat.mtrl-sci*] p. 1-6.

Maclaurin, D. et al. (Jul. 23, 2012). "Nanoscale magnetometry through quantum control of nitrogen-vacancy centres in rotationally diffusing nanodiamonds," arXIV:1207.5276v1 [*quant-ph*] p. 1-9.

Malentinsky, P. et al. (Aug. 22, 2011). "A robust, scanning quantum system for nanoscale sensing and imaging," arXiv:1108.4437v1 [*cond-mat.mes-hall*] p. 1-11.

(56) References Cited

OTHER PUBLICATIONS

Maletinsky. (2012). "A Robust Scanning Diamond Sensor for Nanoscale Imaging with Single Nitrogen-Vacancy Centres," *Nature Nanotechnology* vol. 7: 320-324.

Mamin, H. et al. (Feb. 1, 2013). "Nanoscale Nuclear Magnetic Resonance with a Nitrogen-Vacancy Spin Sensor," *Science* 339: 557-560.

Mamin, H. et al. (Sep. 14, 2012). "Detecting External Electron Spins Using Nitrogen-Vacancy Centers," IBM Research Division, Almaden Research Center, San Jose, CA, p. 1-25.

Meijer, J. et al. (May 1, 2008). "Towards the implanting of ions and positioning of nanoparticles with nm spatial resolution," *Appl. Phys. A* 91:567-571.

Michl, J. et al. (Jan. 16, 2014). "Perfect alignment and preferential orientation of nitrogen-vacancy centers during CVD growth on (111) surfaces," arXiv:1401.4106v2 [*cond-mat.mes-hall*] p. 1-6.

Neumann, P. et al. (Apr. 2, 2013). "High precision nano scale temperature sensing using single defects in diamond,"arXIV:1304.0688v1 [*quant-ph*] p. 1-6.

Pham, L. et al. (Apr. 28, 2011). "Magnetic field imaging with nitrogen-vacancy ensembles," *New Journal of Physics* 13(045021):1-13.

Rondin, L. et al. (Apr. 13, 2012). "Nanoscale magnetic field mapping with a single spin scanning probe magnetometer," arXiv:1108.4438v3 [*cond-mat.mes-hall*] p. 1-10.

Schirhagl, R. et al. (Nov. 12, 2013). "Nitrogen-Vacancy Centers in Diamond: Nanoscale Sensors for Physics and Biology," *Annu. Rev. Phys. Chem.* 2014(65):83-105.

Taylor et al. (2008). "High-Sensitivity Diamond Magnetometer with Nanoscale Resolution," *Nature Physics* vol. 4:810-816.

Taylor, J. et al. (May 9, 2008). "High-sensitivity diamond magnetometer with nanoscale resolution," arXiv:0805.1367v1 [*cond-mat.mes-hall*] p. 1-29.

Tetienne, J-P. (Oct. 19, 2012). "Magnetic-field dependent photodynamics of single NV defects in diamond: An application to qualitative all-optical magnetic imaging," *New Journal of Physics* 14(103033):1-15.

Toyli, D. et al. (Jul. 16, 2012). "Measurement and control of single nitrogen-vacancy center spins above 600K," arXIV:1201.4420v2 [*cond-mat.mes-hall*] p. 1-22.

Toyli, D. et al. (Jul. 23, 2010). "Chip-Scale Nanofabrication of Single Spins and Spin Arrays in Diamond," *Nano Lett* 10:3168-3172.

Toyli, D. et al. (Mar. 27, 2013). "Fluorescence thermometry enhanced by the quantum coherence of single spins in diamond," arXIV:1303.6730v2 [*cond-mat.mes-hall*] p. 1-15.

U.S. Appl. No. 14/542,410, filed Nov. 14, 2014 by Infinitum Solutions, Inc., 53 pages.

Wrachstrup et al. (2009). "Single Spins in Diamond-Probes for Nanoscience," Molecular Imaging, Cornell University, Ithaca, p. 1-27.

\* cited by examiner

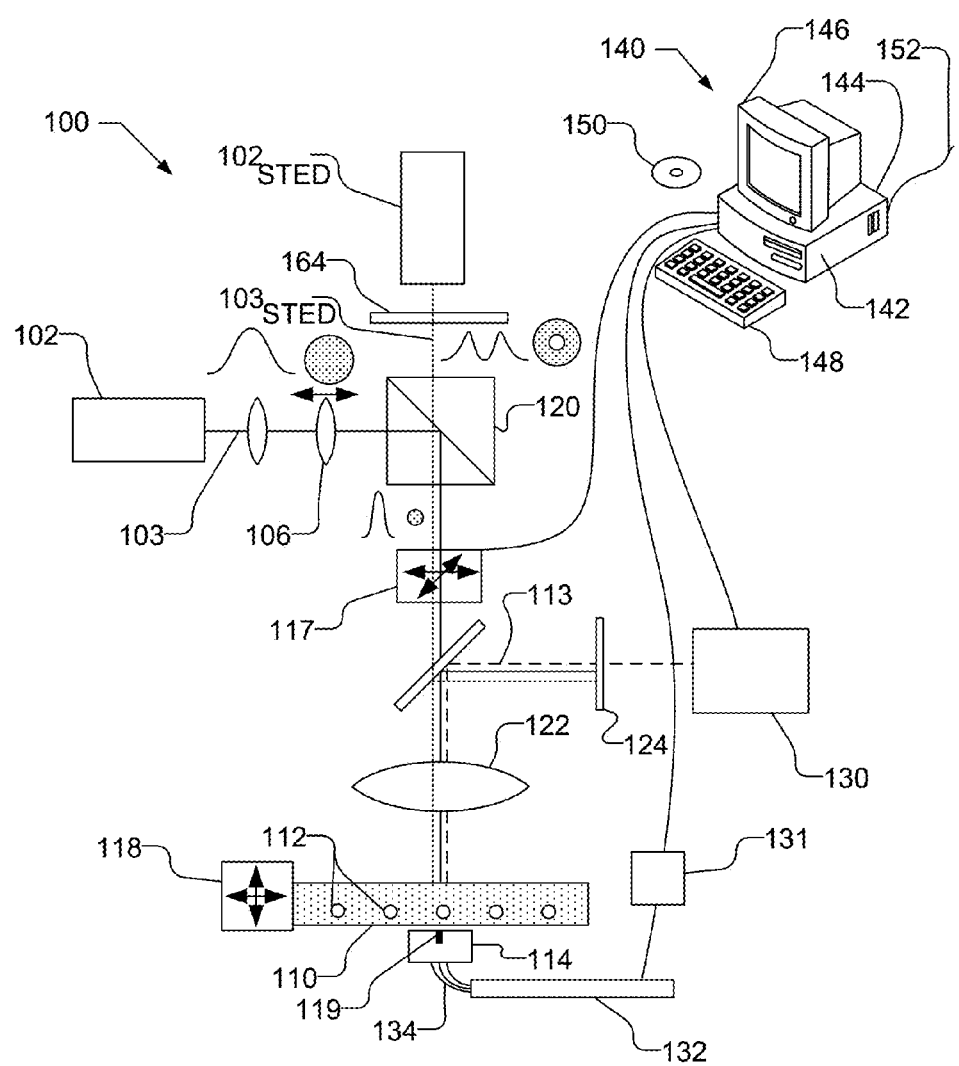
Fig. 26
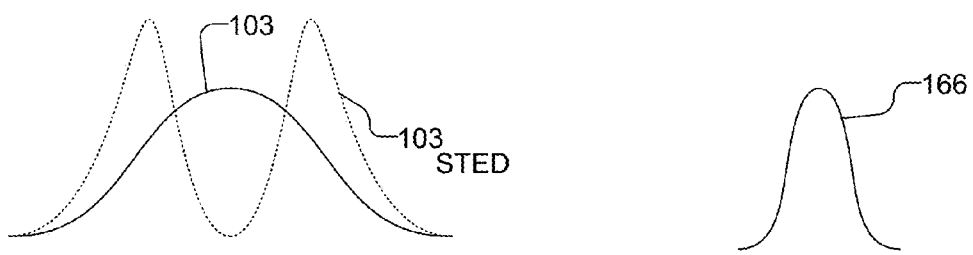
Fig. 27
Fig. 28

INTEGRATED OPTICAL NANOSCALE PROBE

CROSS REFERENCE TO RELATED APPLICATIONS

This application is a continuation-in-part of U.S. application Ser. No. 14/542,410, filed Nov. 14, 2014, and a continuation-in-part of U.S. application Ser. No. 14/532,992, filed Nov. 4, 2014, which is a continuation-in-part of U.S. application Ser. No. 14/184,610, filed Feb. 19, 2014, now U.S. Pat. No. 8,885,301, and claims priority under 35 USC 119 to U.S. Provisional Application No. 61/950,596, filed Mar. 10, 2014, all of which are incorporated by reference herein in their entireties.

BACKGROUND

As critical dimensions in magnetic data storage systems, e.g. hard disk drives, are continuing to shrink to a few tens of nanometers, the development of characterization techniques that may be used in manufacturing or research and development has become increasingly demanding. For example, optical and magneto-optical metrology methods do not provide the spatial resolution required to determine properties of the write-field emanating from the write pole on the nanometer length scale. Magnetic Force Microscopy, on the other hand, has high spatial resolution but does not provide quantitative information about the magnetic field strength. In addition, current magnetic recording heads include other features that are on the nanometer length scale that are desirable to characterize, but that cannot be adequately measured using conventional metrology systems. By way of example, some magnetic recording heads include features such as optical near-field transducers for heat assisted magnetic recording (HAMR), for which characterization of the optical power in the near-field of these near-field transducers is desired. Accordingly, improved metrology methods for characterizing, e.g., magnetic recording heads is desired.

SUMMARY

A diamond probe is suitable to be attached to an Atomic Force Microscope and is created with a tip that incorporates a one or more Nitrogen Vacancy (NV) centers located near the end of the tip. The probe arm acts as an optical waveguide to propagate the emission from the NV center with high efficiency and a beveled end directs excitation light to the NV center and directs photoluminescence light emanating from the NV center into the probe arm. The light source (or a portion of the light source), a detector, as well as an RF antenna, if used, may be mounted to the probe arm. The probe with integrated components enable excitation of photoluminescence in the NV center as well as optically detected Electron Spin Resonance (ODMR) and temperature measurements, and may further serve as a light probe utilizing the physical effect of Stimulated Emission Depletion (STED).

In one implementation, a method includes providing a bias signal to a recording head that includes a write pole to produce a magnetic field from the recording head; scanning a probe having a probe tip comprising at least one nitrogen vacancy center through the magnetic field produced by the recording head; providing an excitation field to the at least one nitrogen vacancy center; producing excitation illumination that is incident on the at least one nitrogen vacancy center; measuring Optically Detected Spin Resonance (ODMR) by detecting a decrease in a spin dependent photoluminescence in response to the excitation illumination caused by electron spin resonance (ESR) of the at least one nitrogen vacancy center; and determining a characteristic of the recording head using the ODMR.

In one implementation, an apparatus includes a biasing source configured to provide a bias signal; a probe card coupled to the biasing source and configured to be connected to a recording head that includes a write pole to provide the bias signal to the recording head that causes the recording head to produce a magnetic field; a probe having a probe tip comprising at least one nitrogen vacancy center, the probe configured to be scanned through the magnetic field produced by the recording head; a light source that produces excitation illumination that is incident on the at least one nitrogen vacancy center; a radio frequency antenna that provides an excitation field to the at least one nitrogen vacancy center; a detector configured to detect photoluminescence produced by the at least one nitrogen vacancy in the probe tip; a processor coupled to the detector and configured to measure Optically Detected Spin Resonance (ODMR) by detecting a decrease in a spin dependent photoluminescence in response to the excitation illumination caused by electron spin resonance (ESR) of the at least one nitrogen vacancy center; and determine a characteristic of the recording head using the ODMR.

In one implementation, a method of determining one or more characteristics of a photon emitter, the method includes producing excitation illumination that is incident on at least one nitrogen vacancy center in a probe tip of a probe, wherein the at least one nitrogen vacancy center produces photoluminescence with an intensity in response to the excitation illumination; producing illumination from the photon emitter, the illumination being incident on the at least one nitrogen vacancy center, wherein the illumination produced by the photon emitter quenches the intensity of the photoluminescence from the at least one nitrogen vacancy center; detecting an amount of quenching of the intensity of the photoluminescence from the at least one nitrogen vacancy center caused by the illumination of the photon emitter; and analyzing the amount of quenching of the intensity of the photoluminescence to determine the one or more characteristics of the photon emitter.

In one implementation, an apparatus for determining one or more characteristics of a photon emitter includes a light source that produces excitation illumination that is incident on at least one nitrogen vacancy center in a probe tip of a probe, wherein the at least one nitrogen vacancy center produces photoluminescence with an intensity in response to the excitation illumination; a detector configured to detect the photoluminescence produced by the at least one nitrogen vacancy center in response to the excitation illumination; a bias source configured to provide bias signals; a probe card coupled to the bias source and configured to be connected to a device that includes the photon emitter, the probe card provides a bias signal to the device that causes the photon emitter to emit illumination that is incident on the at least one nitrogen vacancy center, wherein the illumination produced by the photon emitter quenches the intensity of the photoluminescence from the at least one nitrogen vacancy center; and a processor coupled to control the light source and the bias source and to receive signals from the detector, the processor being configured to determine an amount of quenching of the intensity of the photoluminescence from the at least one nitrogen vacancy center caused by the illumination produced by the photon emitter, and to analyze the amount of quenching of the intensity of the photoluminescence to determine the one or more characteristics of the photon emitter.

BRIEF DESCRIPTION OF THE DRAWINGS

FIG. 26 illustrates an optical metrology device with additional light sources to produce STED illumination to improve resolution and to scan the photon emitter.

FIG. 27 illustrates the Gaussian point spread function of the excitation illumination from the optical metrology device in FIG. 26.

FIG. 28 illustrates the effective point intensity distribution of the excitation illumination combined with the STED illumination.

DETAILED DESCRIPTION

Figure 1:
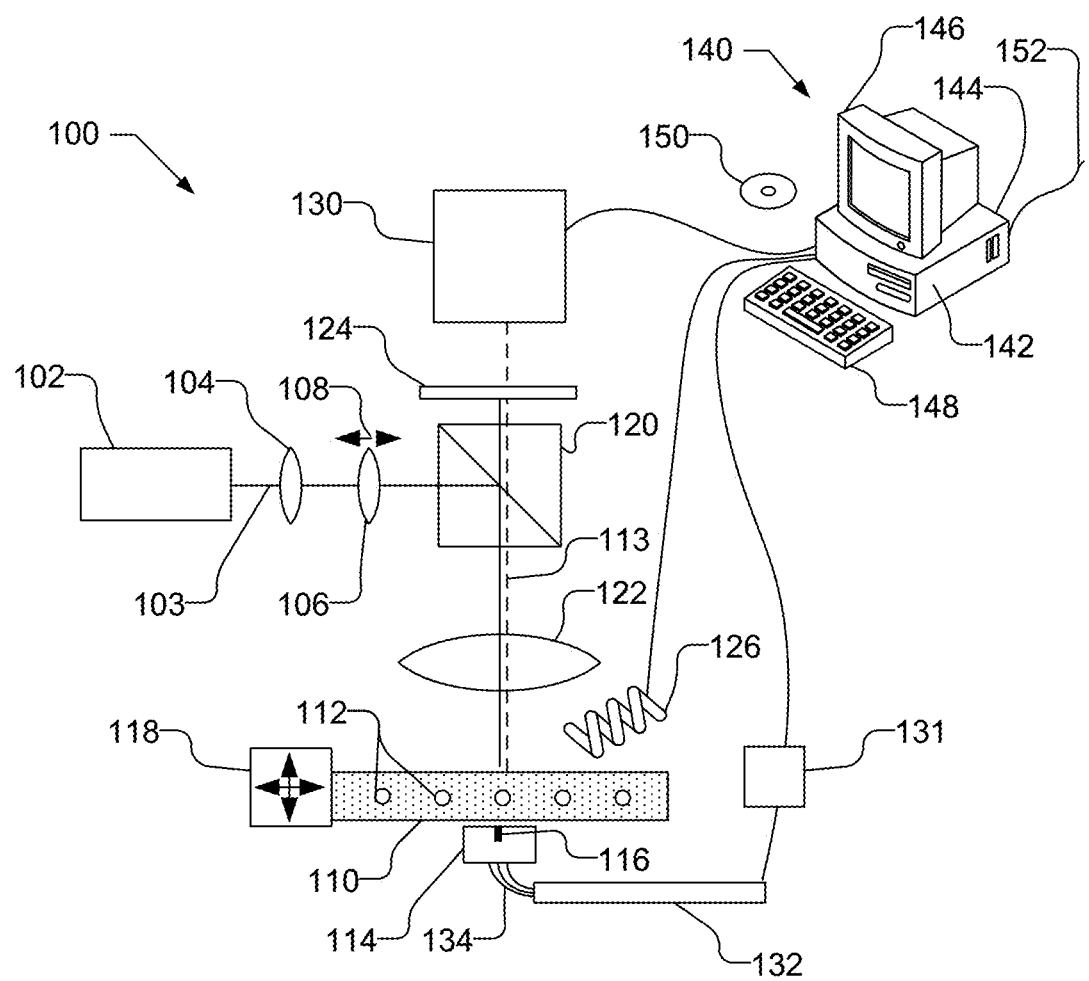
FIG. 1 illustrates an optical metrology device capable of characterizing magnetic recording heads using photoluminescence produced by a substitutional impurity in a crystal.

FIG. 1 illustrates an optical metrology device 100 capable of characterizing magnetic recording heads using photoluminescence produced by a substitutional impurity 112 in a crystal 110. For example, one or more nitrogen vacancy centers (NV centers) in a diamond crystal may be used. An NV center is a naturally occurring or technically created impurity in a diamond crystal where a Nitrogen atom replaces a Carbon atom creating a vacancy next to the Nitrogen atom. The diamond crystal, by way of example, may have a (111) crystal orientation, but other crystalline orientations are possible. If desired, other substitutional impurities in crystals may be used, such as the Silicon-vacancy center in diamond (SiV-), but for the sake of simplicity, the present disclosure will refer to nitrogen NV centers in diamond. The crystal may be, e.g., a crystal film that contains a plurality of NV centers or a crystal particle that contains a single (or a few) NV centers. If desired, a film may be produced that contains a plurality of crystal particles in a suspension forming a film on, e.g. a glass substrate, each crystal particle having one or more NV centers.

The NV centers, which are basically artificial atoms with distinct quantum energy levels, show unique extrinsic and intrinsic optical spin dynamics including stable photoluminescence (PL) based on radiating transitions between optically excited energy levels of their charged quantum states. The PL is temperature as well as magnetic field dependent. Further, Electron Spin Resonance (ESR) is excited in the NV center electronic spin system by an external radio frequency (RF)-field with frequencies resonant with the transitions between the energy sub-levels. At resonance, the PL intensity is measurably reduced. Moreover, the ESR is linearly dependent on an applied magnetic field and, thus, one or more NV centers may be used as a magnetic field sensor with nanometer resolution using optically detected ESR (sometimes referred to herein as ODMR (Optically Detected Magnetic Resonance) (ESR is paramagnetic resonance that falls into this category)). The ESR is also temperature dependent, so that for a fixed applied magnetic field, the shift in ESR is a measure of temperature. For both magnetic field and temperature measurements, the spatial resolution is determined fundamentally by the size of a single NV center which is on the Angstrom length scale. Accordingly, the optical metrology device 100 may optically detect the PL of one or more NV centers 112 in a crystal 110, e.g. using photon counting by employing a photo detector or by using a camera with high sensitivity, to measure a variety of characteristics of a recording head that has features with a nanometer length scale.

The optical metrology device 100 may be, e.g., a microscope such as a confocal microscope or a wide-field microscope. For example, a confocal microscope may include a light source 102 that produces excitation illumination 103 that is incident on the crystal 110 with the substitutional impurities 112. The use of a confocal detection system enables selection of PL coming from only a small volume of the crystal 110, e.g., 1 $\mu m^3$, that is associated with the spot on the surface of the crystal 110 produced by the excitation illumination change. The light source 102 may be, e.g., a laser, light emitting diode (LED), etc., that excites the NV center with a continuous (CW) or pulsed excitation illumination, with one or more wavelengths in a range of 460 nm to 580 nm, and which may be, e.g., 532 nm. With pulsed excitation illumination, the pulse width may be, e.g., approximately 800 ps with a 4-MHz repetition rate. The light source 102 may have a power density of, e.g., 40 kW/cm$^2$, to polarize the NV center by pumping it between the ground and the excited levels. The light from the light source 102 may be provided to a collimator consisting of lenses 104 and 106 either directly or by way of an intervening optical element, e.g., fiber optics or a light pipe. The collimator 104, 106 expands and collimates the light, which is focused by lens 122, which is also used to collect the PL emanating from the NV centers. In an embodiment in which the device is a confocal microscope, the lens 106 (and/or other appropriate lens(es)) may be moved back and forth, as illustrated by arrow 108 and/or a 2-dimensional steering-mirror system could be used to move the excitation illumination 103 relative to the back-aperture plane of the objective lens 122 scanning the focused beam 103 in the sample plane. Additionally, appropriate apertures may be used in an embodiment in which the microscope is a confocal microscope. Moreover, if desired, additional light sources may be used along with light source 102.

A beam splitter 120 receives the excitation illumination from the light source 102 and provides at least a portion of the excitation illumination to the objective lens 122. The excitation illumination is focused on the surface of the crystal 110 by the objective lens 122, which may have a high numerical aperture (NA=0.95) or an oil-immersion lens with an NA of, e.g. 1.3. The objective lens 122 may focus the excitation illumination on the crystal 110 at a normal angle of incidence. It should be understood, however, that an oblique angle of incidence of the excitation illumination may be used if desired. The objective lens 122 focuses the light onto the crystal 110 with one or more NV centers 112. The crystal 110 and NV centers 112 are positioned to be in a magnetic field produced by the recording head 114. The recording head 114 may be a magnetic recording head, such as that used in hard disk drives, and may be in any desired form factor including bar, slider, HGA (head gimbal assembly), and HSA (head stack assembly). Moreover, the recording head 114 may be a Heat Assisted Magnetic Recording (HAMR) write head or other type of magnetic recording head. The crystal 110 may be placed near or in contact with the recording head 114, or if desired, deposited on the recording head 114. Moreover, if desired, an intervening layer may be located between the crystal 110 and the recording head 114, such as a layer of a magnetic recording medium or a layer of material with low thermal conductivity that may be heated by a thermal device on a HAMR write head, or a reflecting layer. The NV centers 112 in the crystal 110 may have a relatively low density such that the distance between adjacent NV centers 112 is greater than a width of the write pole 116 to be measured in the recording head 114. Alternatively, a single NV center 112 may be used in the crystal 110. In such an embodiment, relative movement between the recording head 114 and the crystal 110 may be produced, e.g., as illustrated by actuator 118. Alternatively, the NV centers 112 in the crystal 110 may have a relatively high density such that the distance between adjacent NV centers 112 is similar to or less than the width of the write pole 116 to be measured in the recording head 114. With a relatively high NV center density, relative movement between the crystal 110 and the recording head 114 may not be necessary. Moreover, in some embodiments, movement between the crystal 110 and the recording head 114 may not be possible, for example, if the crystal 110 is applied directly to the recording head 114, e.g., during the manufacturing process. The optical metrology device 100, however, may include additional optic elements to move the excitation illumination over the crystal 110, e.g., in one or two dimensions. In another embodiment, no relative motion is employed, e.g., between the excitation illumination and the crystal or between the crystal and the write pole, but rather the integral ODMR signal is collected for varying excitation fields over an area that includes the write pole, and the magnetic field is derived from the ODMR spectrum using a high density NV film. In another embodiment, the magnetic field produced by the recording head 114 may be varied while maintaining the excitation field constant and the ODMR signal is detected to determine the magnitude of the bias signal necessary to produce a desired magnetic field from the recording head 114. In another embodiment, the thermal device on the recording head 114 may be controlled to vary the heating of the layer of the magnetic recording medium or the layer of material with low thermal conductivity while maintaining the excitation field constant and the ODMR signal is detected to determine the magnitude of the bias signal necessary to produce the desired heating.

During measurement, PL 113 produced by the NV centers 112, illustrated by the dotted line, will be collected by the objective lens 122 and directed by the beam splitter 120 towards a detector 130. As illustrated, a spectral filter 124, such as a dichroic film, is positioned before the detector 130 to remove any reflected excitation illumination and to direct only the PL to the detector 130. The spectral filter 124, thus, may be a long-pass filter with a wavelength cut-off at, e.g., 580 nm, to filter out any remaining pump light. The detector 130 may be, e.g., a non-imaging photodetector, such as a silicon avalanche photodiode operating in the signal photon regime, which detects the optical intensity at a single spot. Alternatively a CCD camera can be used to detect the PL.

In addition, a radio wave frequency (RF) antenna 126 is positioned to provide an excitation field to the crystal 110. The RF antenna 126 may produce a varying excitation field, e.g., that may be controlled to sweep the frequency in a continuous or stepped manner. A continuous or pulsed excitation field produced by the RF antenna 126 may have a power of, e.g., 1 W and a frequency ranging from 1 GHz to 5 GHz. The RF antenna 126 may also produce a constant excitation field. The excitation field produced by RF antenna 126 drives electron spin resonance which may be optically detected, e.g., ODMR, by detecting a drop in the spin dependent PL in response to the excitation illumination caused by electron spin resonance (ESR) of the nitrogen vacancy centers. The ODMR may be detected while varying the excitation frequencies of the excitation field while holding the magnetic field produced by the recording head 114 constant, while holding the excitation frequency of the excitation field constant while varying the magnetic field produced by the recording head 114, or while varying both the excitation frequencies of the excitation field and the magnetic field produced by the recording head 114.

The detector 130 is connected to a computer 140 and the computer 140 receives, stores, and analyzes the optically detected data provided by the detector 130, along with the excitation frequencies provided by RF antenna 126 associated with the data. The computer 140 includes a processor 142 with memory 144, as well as a user interface including e.g., a display 146 and input devices 148. A non-transitory computer-usable storage medium 150 having computer-readable program code embodied may be used by the computer 140 for causing the processor 142 to control the optical metrology device 100 and to perform the functions including the analysis described herein. The data structures and software code for automatically implementing one or more acts described in this detailed description can be implemented by one of ordinary skill in the art in light of the present disclosure and stored, e.g., on a computer readable storage medium 150, which may be any device or medium that can store code and/or data for use by a computer system such as processor 142. The computer-usable storage medium 150 may be, but is not limited to, magnetic and optical storage devices such as disk drives, magnetic tape, compact discs, and DVDs (digital versatile discs or digital video discs). A communication port 152 may also be used to receive instructions that are used to program the computer 140 to perform any one or more of the functions described herein and may represent any type of communication connection, such as to the internet or any other computer network. Additionally, the functions described herein may be stored in memory 155 or embodied in whole or in part within the circuitry of an application specific integrated circuit (ASIC) or a programmable logic device (PLD), and the functions may be embodied in a computer understandable descriptor language which may be used to create an ASIC or PLD that operates as herein described.

As illustrated, the computer 140 may be coupled to the recording head 114, via a probe card 132 which is connected to the recording head 114 using one or more probes 134, which may be, e.g., pogopins, probes, or other contacts such as wires that are wire bonded. The probe card 132 may be coupled to a biasing source 131 that provides a bias signal, such as a current or voltage signal, which is provided to the recording head 114 via the probe card 132 and causes the recording head 114 to produce a magnetic field. The biasing source 131 may be connected to and controlled by the computer 140. The computer 140, thus, may control the magnetic field produced by the recording head 114, e.g., by controlling the bias signal provided to the recording head. The biasing source 131 may provide a plurality of bias signals with different levels to the recording head 114. Accordingly, the recording head 114 may be controlled via the biasing source 131 to produce a constant magnetic field, e.g., while the excitation field is varied, or to produce a varying magnetic field, while the excitation field is held constant (or varied). The varying magnetic field produced by the recording head 114 may vary continuously or in a stepped manner. The computer 140 may cause the biasing source 131 (or another biasing source) to further control any other desired features of the recording head 114, such a thermal device, e.g., a high intensity light source, on the recording head 114, when the recording head 114 is, e.g., a HAMR write head. Accordingly, the recording head 114 may be controlled via the biasing source 131 to produce a constant heat level, e.g., while the excitation field is varied, or to produce varying heat levels, while the excitation field is held constant (or varied). Additionally, when the recording head 114 includes a Dynamic-Flying Height (DFH) device, one of the probes 134 of the probe card 132 may be used to provide current to the microactuator device from a second circuit in the current or voltage source that is connected to the computer 140. Write heads use a DFH device as an adjustment mechanism to internally bias the write pole closer to or further from the air bearing surface. The DFH device is typically in the form of a heater incorporated into the write head structure, with additional contact pads for external connection. By applying a bias to the additional contact pads via the probe card 132, the position of the write pole can be adjusted towards or away from the air bearing surface of the write head. By adjusting the position of the write pole via the DFH device, the recording head 114 may be measured at different temperatures and/or vertical displacement from the crystal 110.

Additionally, when the recording head 114 includes a microactuator device, one of the probes 134 of the probe card 132 may be used to provide current to the microactuator device. The source of the current may be a second circuit in the current or voltage source connected to the computer 140. Write heads use a microactuator device as an adjustment mechanism to move the write pole in the cross-track direction to better align the write pole to the lands of a disk that is being written to. The microactuator device is incorporated into the write head structure, which includes additional contact pads for external connection. By applying a bias to the additional contact pads via the probe card 132, the position of the write pole can be adjusted in the cross-track direction. By adjusting the position of the write pole via the microactuator device during measurement with the device, the performance of the microactuator may be verified and the characteristics of the recording head 114 may be measured at different write pole positions.

The computer 140 is further coupled to control the RF antenna 126 to provide a desired excitation field (or varying excitation field) to the crystal 110 during measurement.

As discussed above, an NV center in diamond is a naturally occurring or technically created impurity in a diamond crystal where a Nitrogen atom replaces a Carbon atom creating a vacancy next to the Nitrogen atom. Nitrogen vacancy centers may be created in a diamond crystal, e.g., using a type-Ib HPHT single-crystal sample that is initially embedded with nitrogen impurities. For example, nitrogen impurities may be embedded by irradiation with a an ion-beam, e.g. $N_2^+$ ions at 5 keV, in case of a very high purity diamond film or by an electron beam in case the diamond film already has nitrogen impurities and annealing, e.g., for 2 hours at 850° C. The density of the NV centers within the crystal film may be controlled, e.g., by controlling the applied irradiation dose, or using appropriate masking techniques. For example, an ion beam fluence of $10^{11}$ cm$^2$ can result in density of $8 \times 10^{10}$ NV cm$^{-2}$. Moreover, by controlling the energy of the implantation as well as the annealing process the depth of the NV centers implanted in the crystal may be controlled.

Figure 2:
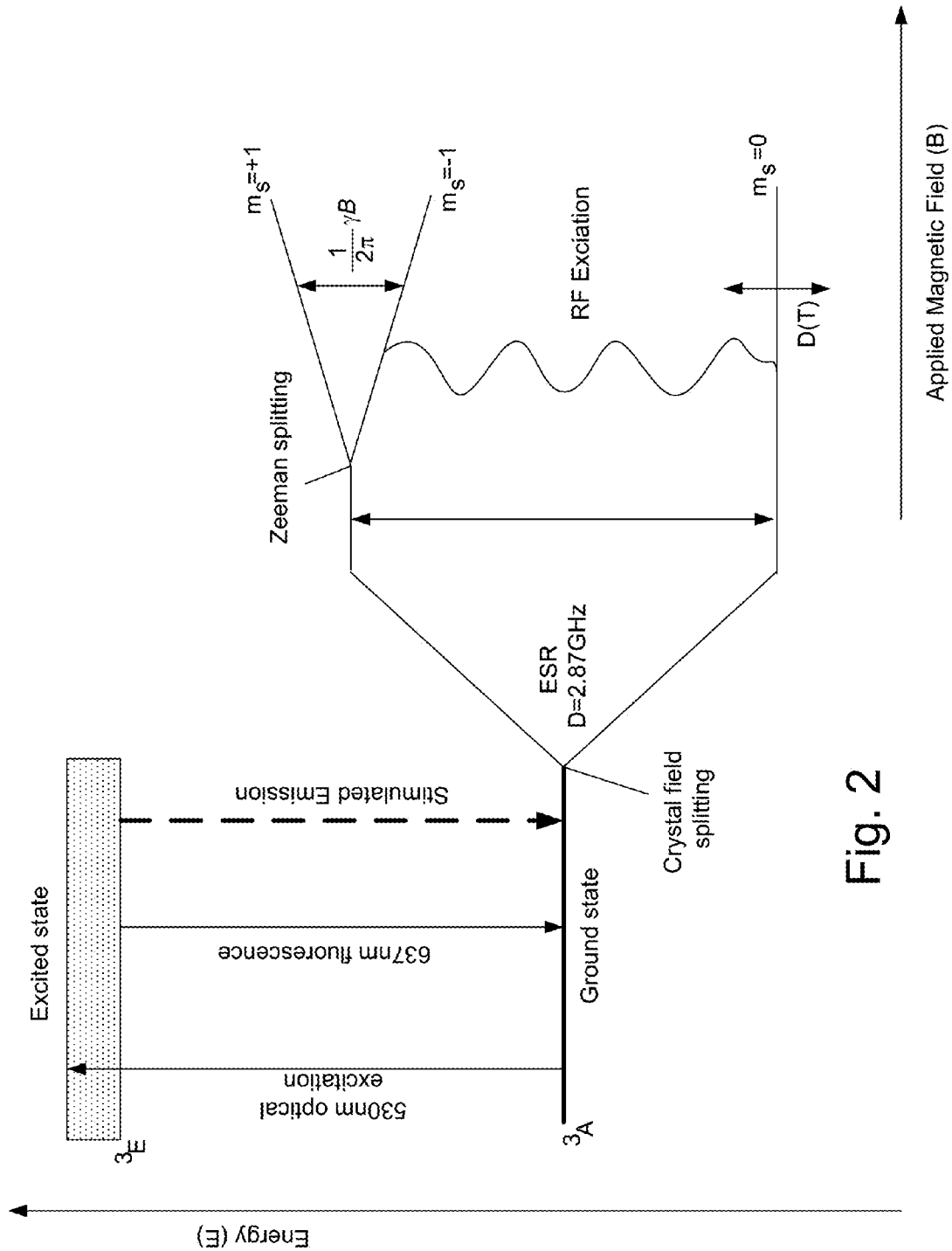
FIG. 2 schematically illustrates the energy levels of a negatively charged nitrogen vacancy center in a diamond crystal.

FIG. 2 schematically illustrates the energy levels of a negatively charged NV center in a diamond crystal. An NV center may be optically excited, e.g., with excitation illumination having a wavelength range from 460 nm to 580 nm, which yields an intense fluorescence emission from the NV center with lifetimes in the millisecond range. For example, as illustrated, the NV center may be excited with a laser at a wavelength of 532 nm and in response will emit a broadband luminescence with a zero phonon line at 637 nm, at room temperature. FIG. 2 further illustrates the mechanism of stimulated emission, in which an electron in an excited state gives energy to an incoming photon and is forced to the ground state before it can create photoluminescence by spontaneous emission. The ground state of the NV center has an electron spin triplet structure with a zero-field frequency splitting of 2.87 GHz between the $m_S=0$ and the degenerate $m_S=\pm 1$ states. In the absence of an external magnetic field, e.g., from the recording head 114, a drop of luminescence intensity is present at an excitation frequency of 2.88 GHz due to the induced change in populations of $m_S=0$ and $m_S=\pm 1$ spin sublevels. Thus, the location of the NV center may be identified by an optically detected zero field magnetic resonance at ~2.88 GHz which has its origin in the crystal-field splitting of energy sublevels. The magnetic resonance occurs between the $m_s=0$ and $m_s=\pm 1$ spin sub-levels of the spin triplet ground state $^3A_2$ and can be detected by either conventional electron paramagnetic resonance (EPR) or optically detected magnetic resonance (ODMR). The optical detection of the magnetic resonances of the NV center is enabled by the differing fluorescence of the $m_s=0$ and $\pm 1$ spin projections, i.e. the fluorescence intensity is reduced when the spin system is in resonance due to the RF excitation.

In the presence of a magnetic field from the recording head 114, the resonance peak will split due to the Zeeman effect. As illustrated in FIG. 2, two resonance peaks may be identified, respectively corresponding to transitions between $m_S=0$ and $m_S=-1$, and between $m_S=0$ and $m_S=+1$ sublevels. The frequency of these resonance peaks is a function of the magnitude of the magnetic field and is called the Larmor frequency f given by $$f = \frac{1}{2\pi}\gamma B \quad \text{eq. 1}$$

where γ is the Gyromagnetic ratio and B the magnetic field, i.e. by measuring f, the magnetic field B may be determined. Thus, for magnetic field sensing applications, the magnetic field may be evaluated by measuring the Zeeman shifts of the NV center defect electron spin sub-levels through the optical detection of electron spin resonance (ESR), i.e., ODMR. The ODMR may be measured by detecting a decrease in the spin dependent PL caused by ESR of the NV centers while varying the excitation frequencies of the excitation field while holding the magnetic field produced by the recording head 114 constant, while holding the excitation frequency of the excitation field constant while varying the magnetic field produced by the recording head 114, or while varying both the excitation frequencies of the excitation field and the magnetic field produced by the recording head 114. One of the advantages of the use of NV center-based magnetometry is the possible combination of atomic-scale spatial resolution with high magnetic field sensitivity, e.g., below 10 nT Hz$^{-1/2}$, even under ambient conditions.

As illustrated in FIG. 2, the $m_S=0$ spin state is dependent on temperature D(T), and consequently the ESR frequency is temperature dependent. Moreover, the PL intensity ($I_{PL}$) of an NV center and the relative $I_{PL}$ difference between its spin states (ESR contrast), which strongly decrease above 550° K, may be used to measure temperature. Accordingly, one or more NV centers may serve as a nano-scale thermometer with sensitivities on the order of 100 mK/Hz between room temperature and 700° K. The high sensitivity and wide range of operating temperatures make NV centers an attractive candidate for a variety of thermo-sensing applications such as diamond-based scanning thermal microscopy. The impact of temperature versus magnetic field on the ESR spectrum may be distinguished using a pulsed RF excitation field with an appropriate pulse sequence (spin echo technique), as opposed to a continuous-wave RF excitation field. The thermal device of the recording head 114 may be controlled via the biasing source 131 to produce a constant temperature while the excitation frequency of the excitation field is varied or to produce different temperatures while holding the excitation frequency of the excitation field constant, or while varying both the temperature produced by the thermal device of the recording head 114 and the excitation frequencies of the excitation field.

In addition, the PL of an NV center may be turned "off" in time, when the 532 nm excitation pulse, e.g., with a duration of 60 ps, is followed by a longer wavelength pulse e.g. 775 nm and duration 3.2 ns, of sufficient intensity. This mechanism is known as Stimulated Emission Depletion (STED). Alternatively, STED with CW or quasi CW illumination may be employed. Spatial resolution may be improved using STED to functionally switch off a portion of NV centers, e.g., STED microscopy.

Additionally, if desired, Ground State Depletion (GSD) may be used, as opposed to STED. Similar to STED, GSD uses depletion illumination to functionally switch off a portion of NV centers, but unlike STED, GSD uses the same wavelength for the excitation illumination and the depletion illumination.

Thus, one or more NV centers in a diamond film may be used to measure the write field of a recording head with nano-meter spatial resolution making use of the optically detected Electron Spin Resonance (ODMR), which frequency spectrum depends linearly on the magnetic field. Accordingly, characteristics of the recording head, including efficiency of the recording head, the strength of the magnetic field and physical dimensions of the write pole may be measured. This may be carried out by exercising the write portion of the recording head with a write current, which can be a DC or an AC current, to produce the magnetic field at the write pole. For example, the efficiency of the recording head may be determined by varying the bias signal to the recording head to vary the magnetic field while maintaining the excitation field at a constant frequency to determine the relationship between the applied bias signal and resulting magnetic field as provided by equation 1. In another example, the strength of the magnetic field may be determined for any scanned position based on the frequency of these resonance peaks, as provided by equation 1. Additionally, one or more NV centers in a diamond film may be used to measure the near-field power of a near-field transducer in a recording head used in thermally assisted magnetic recording with nano-meter spatial resolution making use of temperature dependence of the optically detected Electron Spin Resonance or the temperature dependency of the PL intensity. Moreover, the efficiency of the thermal device in the recording head may be determined by varying the bias signal to the thermal device to vary the temperature while maintaining the excitation field at a constant frequency to determine the relationship between the applied bias signal and resulting heat.

Thus, a characteristic of the recording head 114 may be determined based on the ESR as measured by the detector 130, the frequency of excitation field produced by RF antenna 126, and the bias applied to the recording head 114 by the biasing source 131 to control the magnetic field and/or the heat produced by the thermal device. For example, a graph may be generated for the excitation field with respect to the bias signal. The excitation field may be fixed and the bias signal may be swept to vary the magnetic field or heat produced by the recording head, or the bias signal may be fixed and the excitation field swept. This process may be repeated at multiple levels of the fixed excitation field or the fixed bias signal and the magnetic field determined from the ESR, e.g., based on equation 1. Additionally, an external thermal device may be used to calibrate the ESR with respect to heat for one or more excitation frequencies of the RF antenna 126, and the heat produced by, e.g., a HAMR recording head 114, at one or more bias levels may be determined by measuring the ESR.

Figure 3:
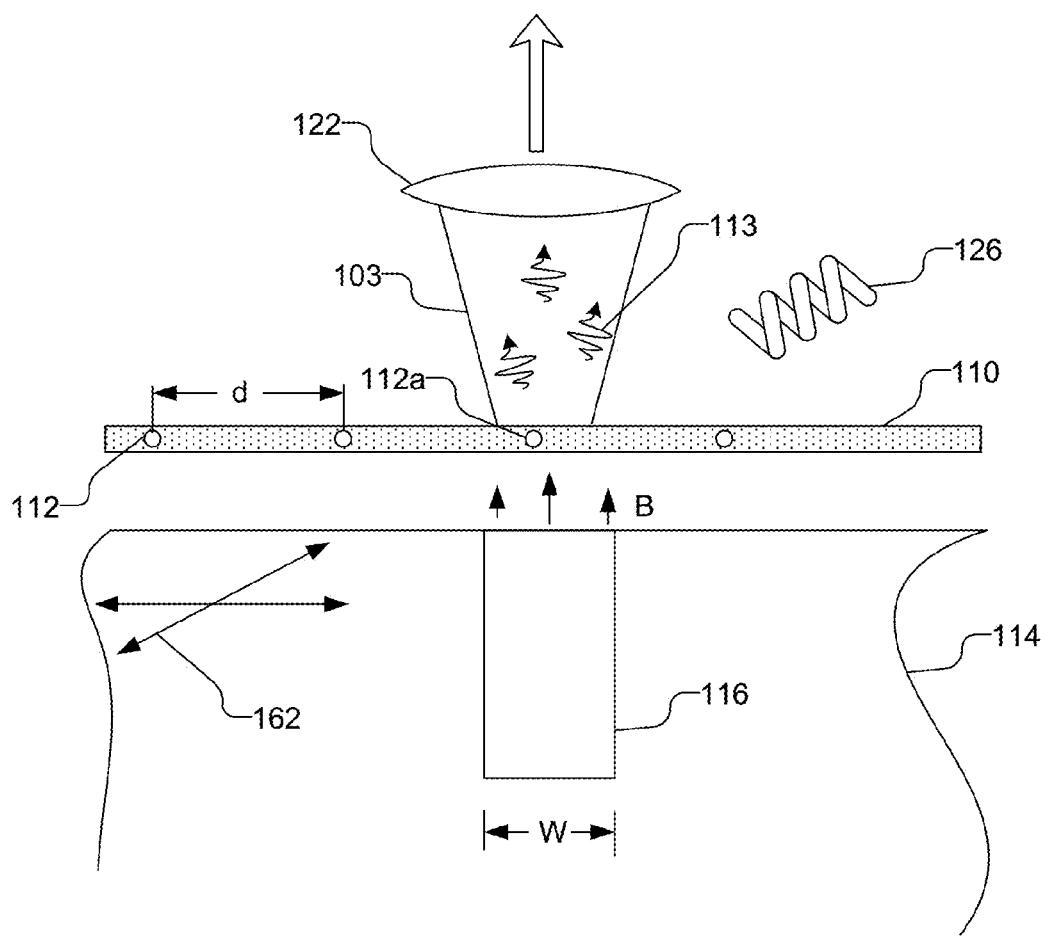
FIG. 3 schematically illustrates a diamond film with a plurality of nitrogen vacancy centers that is positioned to be in a magnetic field produced by a write pole from a recording head.

FIG. 3, by way of example, schematically illustrates a diamond film 110 with a plurality of NV centers 112 and that is positioned to be in a magnetic field B produced by a write pole 116 from a recording head 114. As discussed above, a light source 102 (shown in FIG. 1) produces excitation illumination 103 that is focused by objective lens 122 onto the diamond film 110 while an external RF excitation field is produced by the RF antenna 126 with varying excitation frequencies or pulse sequence. In response to the excitation illumination 103, the NV center 112a produces spin dependent PL 113 that is collected by the objective lens 122 and provided to the detector 130 (shown in FIG. 1). The Optically Detected Spin Resonance (ODMR) may be measured by detecting a decrease in the spin dependent PL 113 caused by electron spin resonance (ESR) of the NV centers at varying excitation frequencies of the excitation field. If desired, the magnetic field of the recording head 114 may be varied while maintaining a constant frequency of the excitation field (or varying the frequency of the excitation field) while measuring ODMR.

As illustrated in FIG. 3, the write pole 116 has a width W, while the density of the NV centers 112 in the diamond film 110 is such that adjacent NV centers are separated by a distance d that is greater than the width W of the write pole 116, i.e., d>W. In such a configuration, a single NV center may be positioned over the write pole 116, as illustrated. Relative movement between the recording head and the diamond film 110 may be produced in two dimensions, e.g., by moving the recording head with respect to the diamond film 110, thereby scanning a single NV center over the recording head in two dimensions, as illustrated by arrows 162. The ODMR may be measured by detecting a decrease in the spin dependent PL 113 caused by electron spin resonance (ESR) of a single NV center at varying excitation frequencies of the excitation field and/or varying magnetic fields of the recording head as the NV center is scanned over the recording head in two dimensions. Accordingly, characteristics of the recording head 114 may be measured with nano-meter spatial resolution including the efficiency of the recording head, dimensions of write pole 116 and strength of the magnetic field B.

Figure 4:
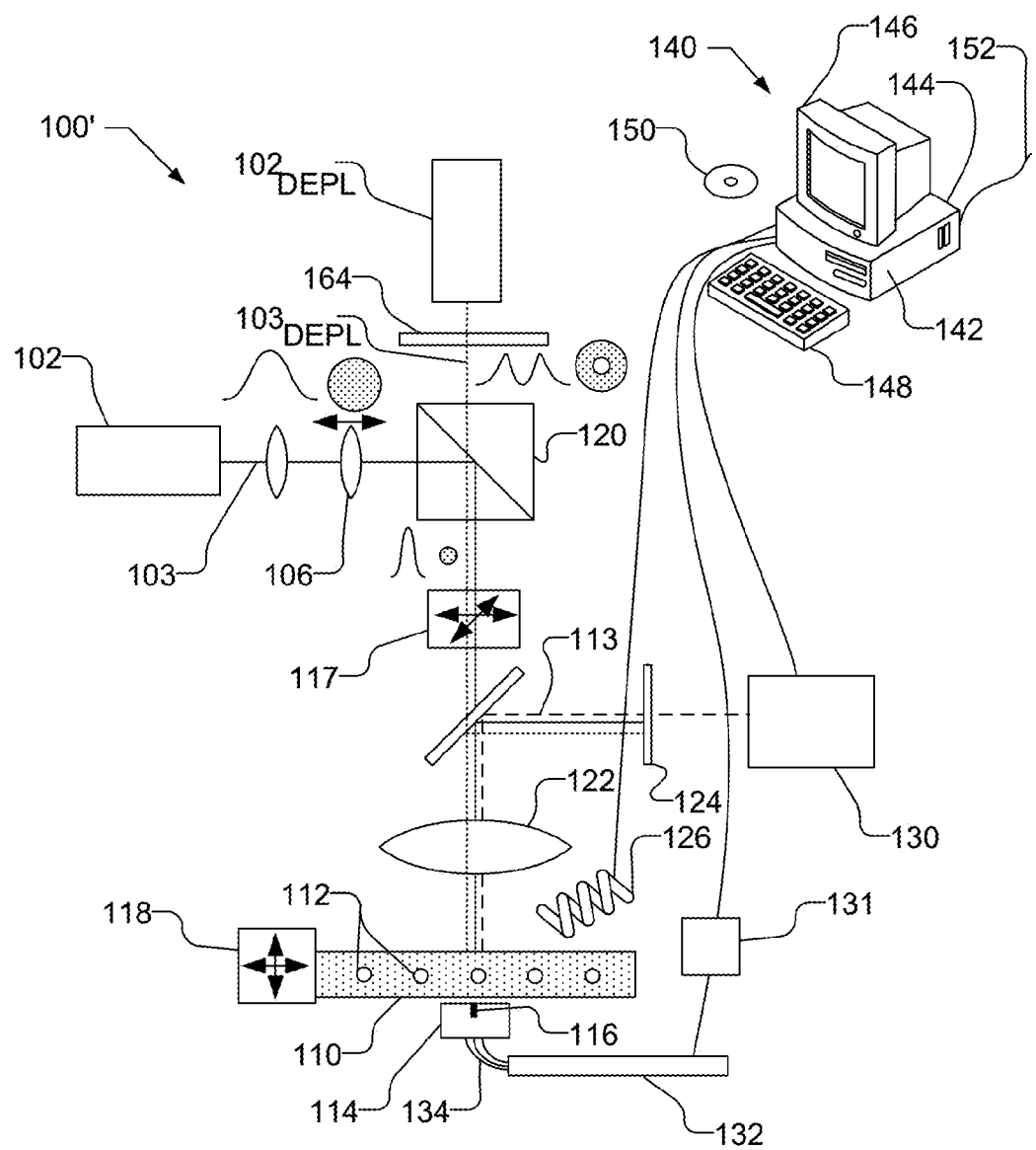
FIG. 4 illustrates an optical metrology device that uses Stimulated Emission Depletion.
Figure 5:
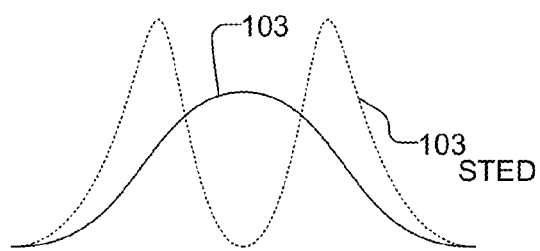
FIG. 5 illustrates the point spread function of excitation illumination and depletion illumination.
Figure 6:
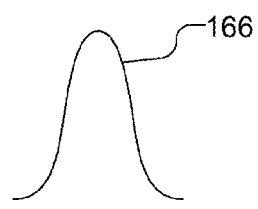
FIG. 6 illustrates the effective point spread function of the combined excitation illumination and depletion illumination from FIG. 5.

FIG. 4 illustrates an optical metrology device 100' that is similar to the optical metrology device 100, shown in FIG. 1, like designated elements being the same, but that uses Stimulated Emission Depletion (or GSD) as discussed above. As illustrated, optical metrology device 100' includes a second light source $102_{DEPL}$ that produces depletion illumination $103_{DEPL}$, with the same or different wavelength in the case of GSD or STED, respectively, and that is coincident on the diamond film 110 with the excitation illumination 103 from light source 102. The light source 102 produces excitation illumination 103 that has a Gaussian point spread function and produces a relatively large diffraction limited spot on the diamond film 110. FIG. 5, by way of example, illustrates the Gaussian point spread function of the excitation illumination 103 with a solid line. The second light source $102_{DEPL}$ produces light that passes through a vortex phase plate 164 to produce a ring shaped beam that has a central zero intensity at the focal plane. FIG. 5, by way of example, illustrates a ring shaped point spread function distribution of the depletion illumination $103_{DEPL}$ which is coincident with the excitation illumination 103. The depletion illumination $103_{DEPL}$ quenches PL in the NV centers 112 in the diamond film 110 that are off-center, so that the off-center NV centers only contribute a constant background, which may be subtracted from the ODMR signal, thereby providing a signal from only the NV centers in the center of the depletion illumination $103_{DEPL}$. FIG. 6 illustrates the effective point spread function 166 of the combined excitation illumination 103 combined with the depletion illumination $103_{DEPL}$. The coincident excitation illumination 103 and depletion illumination $103_{DEPL}$ may be scanned over the diamond film 110 to measure characteristics of the recording head 114 in two dimensions, e.g., using one or more mirrors 117 in the beam path.

In the case of using GSD, the depletion illumination $103_{DEPL}$ may have a wavelength of 532 nm, with increased power. For example, a reduction in the photoluminescence may be achieved for depletion illumination $103_{DEPL}$ with power greater than 2 MW/cm$^2$. The depletion illumination $103_{DEPL}$ may be continuous (CW) or pulsed excitation, with a pulse width of, e.g. 150 ps, where a pulsed depletion illumination $103_{DEPL}$ results in stronger photoluminescence reduction.

Figure 7:
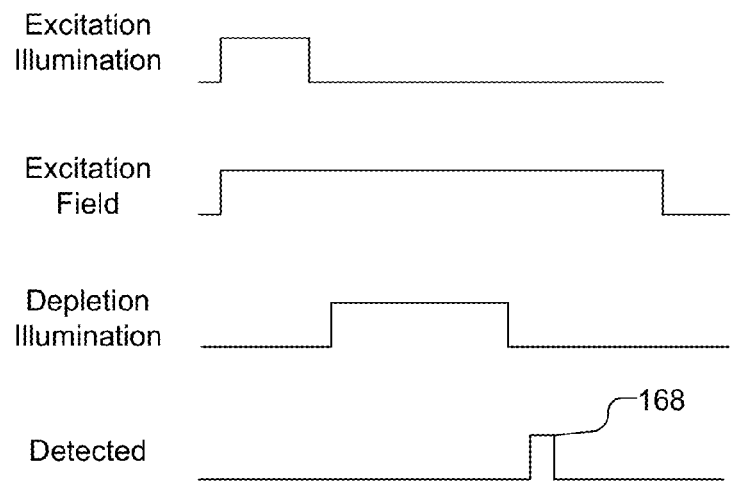
FIG. 7 illustrates several waveforms used to measure Optically Detected Spin Resonance using depletion illumination.

FIG. 7, by way of example, illustrates several waveforms that may be used to measure ODMR using depletion illumination. As illustrated, a pulse of excitation illumination is provided along with the excitation field and followed by a pulse of depletion illumination. The RF excitation field need not be pulsed and may always be on, and one or both of the excitation field and the magnetic field produced by the recording head 114 may be varied. The intensity of the depletion illumination is much greater than the intensity of the excitation illumination in the case of case of GSD or has a longer wavelength in case of STED. The PL signal 168 is detected after the pulsed depletion illumination.

Figure 8:
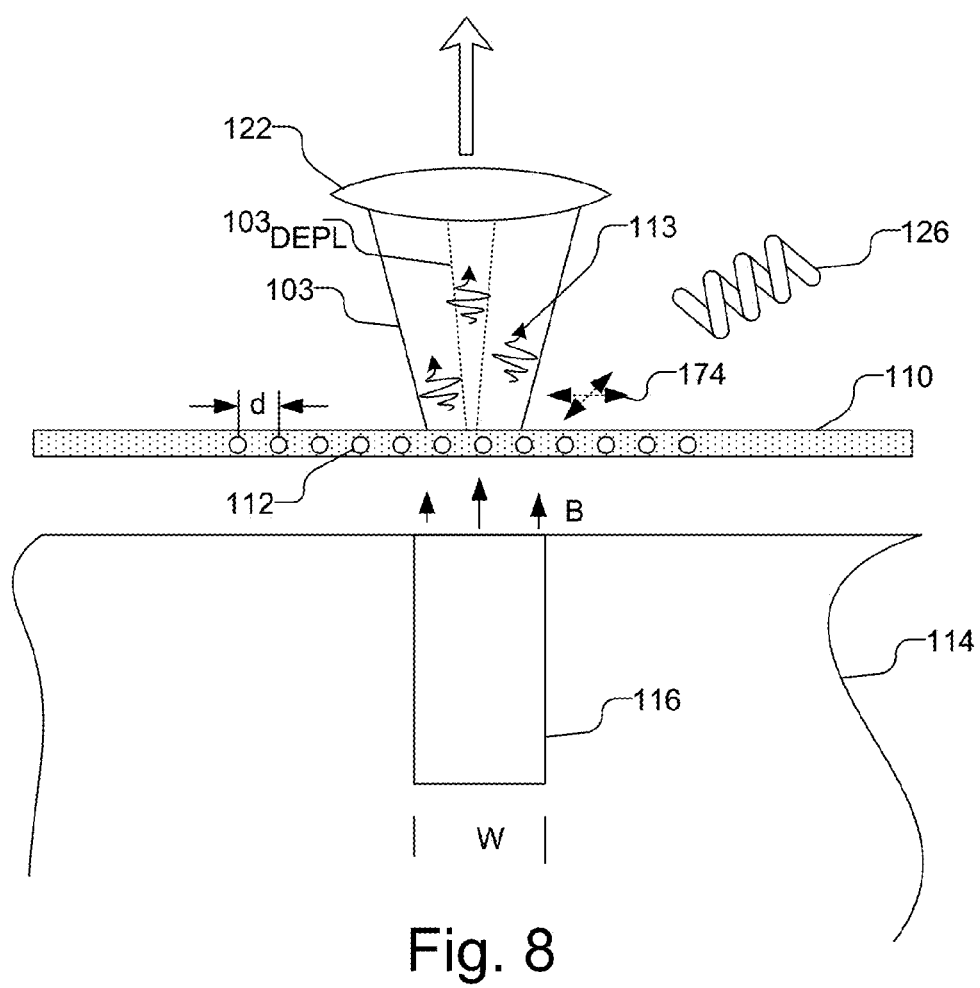
FIG. 8 schematically illustrates the use of depletion illumination to measure Optically Detected Spin Resonance from a diamond film with a plurality of nitrogen vacancy centers that is positioned to be in a magnetic field produced by a write pole from a recording head.

FIG. 8 schematically illustrates the measurement of ODMR from a diamond film 110 with NV centers 112 similar to FIG. 3, but uses depletion illumination $103_{DEPL}$, e.g., for either STED or GSD, and the diamond film 110 has an increased density of NV centers 112. As illustrated in FIG. 8, the density of the NV centers 112 in the diamond film 110 may be such that adjacent NV centers are separated by a distance d that is less than the width W of the write pole 116, i.e., d<W. The density of NV centers may be chosen so that a plurality of NV centers, e.g. 10×10 NV centers, is located under the write pole 116. The coincident excitation illumination 103 and depletion illumination $103_{DEPL}$ enables a reduced number of NV centers to be resolved, e.g., only NV centers that fall within the ring minimum of the depletion illumination $103_{DEPL}$ are resolved. The coincident excitation illumination 103 and depletion illumination $103_{DEPL}$ may be scanned in two dimensions over the diamond film, as illustrated by arrows 174, e.g., using an arrangement of mirrors in the beam path, thereby obviating the needs for an actuator to produce relative movement between the recording head and the diamond film 110. The ODMR may be measured by detecting a decrease in the spin dependent PL 113 caused by electron spin resonance (ESR) of the NV center(s) that fall within the ring minimum of the depletion illumination $103_{DEPL}$ at varying excitation frequencies of the excitation field and/or varying magnetic fields produced by the recording head 114 as excitation illumination 103 and depletion illumination $103_{DEPL}$ are scanned over the recording head in two dimensions. Accordingly, characteristics of the recording head may be measured with nano-meter spatial resolution including dimensions of write pole 116 and strength of the magnetic field B.

Figure 9:
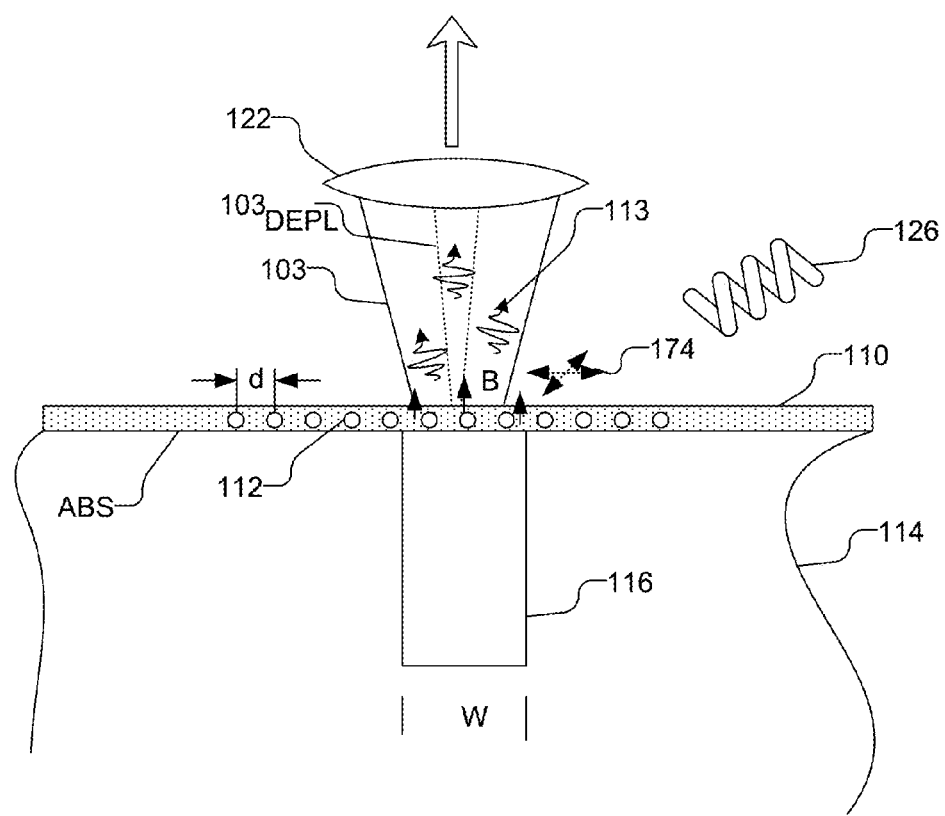
FIG. 9 schematically illustrates the use of depletion illumination to measure Optically Detected Spin Resonance from a diamond film with a plurality of nitrogen vacancy centers that is in contact with the air bearing surface of the recording head.

If desired, the diamond film 110 may be in direct contact with the recording head 114, e.g. in contact with the Air Bearing Surface (ABS) of the recording head. For example, a diamond film 110 with a relatively high density of NV centers 112, e.g., such that there are a plurality of NVC centers located under the write pole, may be directly deposited on the ABS of the recording head. FIG. 9 schematically illustrates the measurement of ODMR from a diamond film 110 with NV centers 112, similar to that shown in FIG. 8, but with the diamond film 110 attached to the ABS of the recording head 114, i.e., directly coupled to or coupled to with one or more intervening layers. As discussed above, the coincident excitation illumination 103 and depletion illumination $103_{DEPL}$ may be scanned with respect to the recording head in two dimensions to measure ODMR at varying excitation frequencies of the excitation field and/or varying magnetic fields produced by the recording head 114 as excitation illumination 103 and depletion illumination $103_{DEPL}$ are scanned over the recording head in two dimensions.

Figure 10:
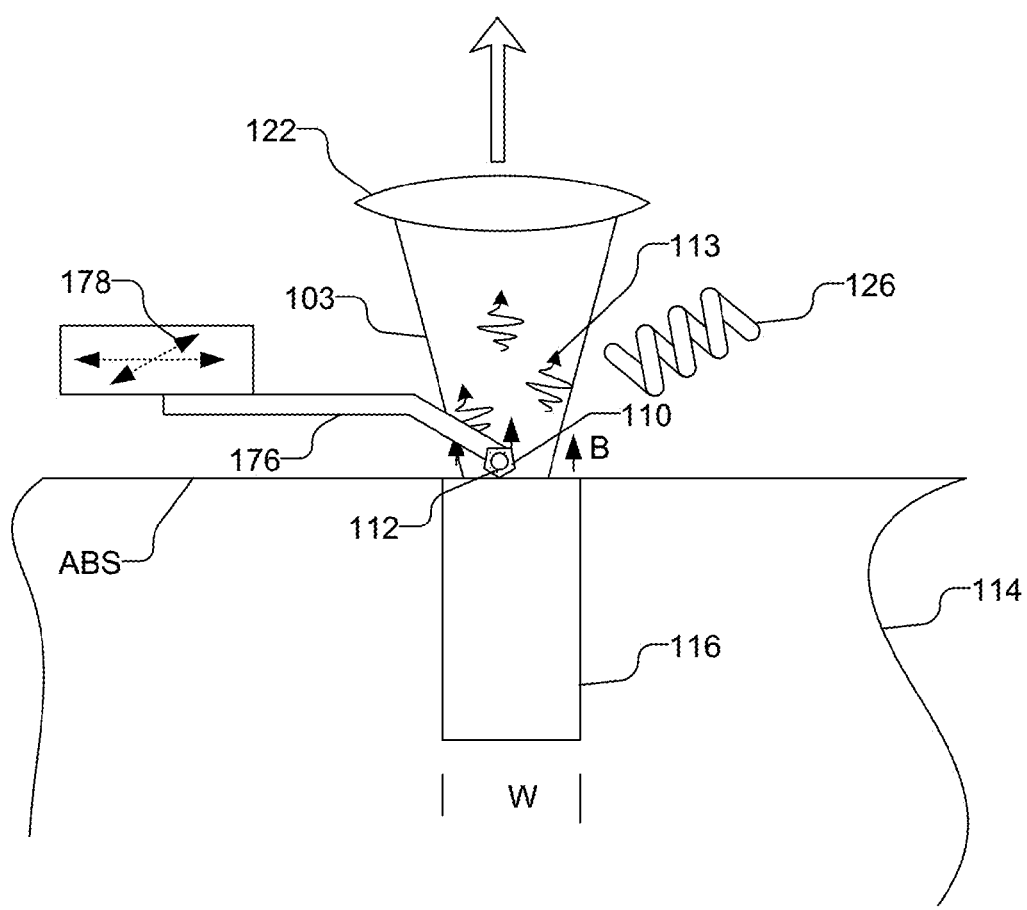
FIG. 10 schematically illustrates a diamond film with a nitrogen vacancy center that is on an Atomic Force Microscope arm positioned to be in a magnetic field produced by a write pole from a recording head.

FIG. 10 is similar to FIG. 3 and schematically illustrates the measurement of ODMR from a diamond film 110 with an NV center 112 held on the tip of an Atomic Force Microscope (AFM) arm 176 and that is in contact with the ABS of the recording head 114. As illustrated, the diamond film 110 may be a micron sized diamond particle that includes a single or several NV centers 112. The AFM arm 176 is scanned over the recording head 114 in two dimensions, as illustrated by arrows 178 and the PL 113 from the NV centers is collected. The ODMR may be measured from the NV center(s) 112 in the diamond film 110 positioned at the tip of the AFM arm 176, at varying excitation frequencies of the excitation field and/or varying magnetic fields produced by the recording head 114 as the AFM arm 176 is scanned over the recording head in two dimensions.

Figure 11A:
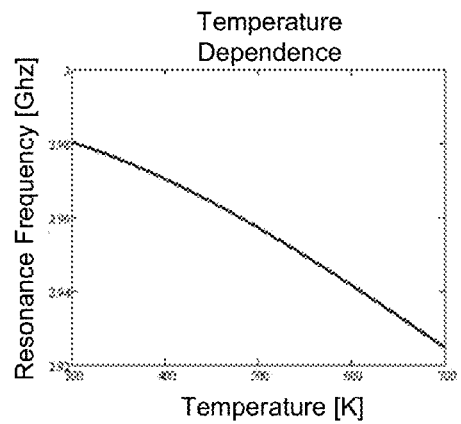
FIGS. 11A and 11B illustrate the temperature dependence of the ESR frequency and resulting resonance lines at different temperatures, e.g., 300° K and 700° K.
Figure 11B:
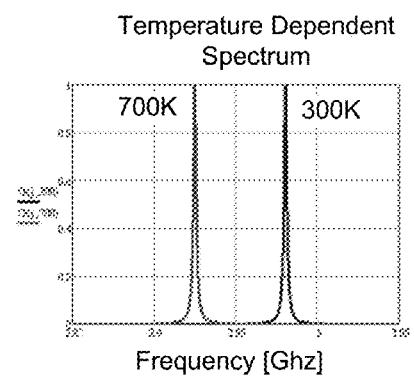

In addition to measuring characteristics such as physical dimensions of the write pole 116 and the strength of the magnetic field B, the NV centers 112 in a diamond film may be used to measure the heat produced by a bias controlled thermal device. In one embodiment, for example, the near-field power at the near-field transducer of a write head for Heat-Assisted Magnetic Recording (HAMR) may be tested, but it should be understood that characteristics of any device that produces heat using a bias controlled thermal device may be measured. Characteristics related to the thermal device that may be determined include, e.g., power, temperature with respect to bias signal, spatial extent of the thermal device, or near-field transducer, and heating characteristics such as the spatial extent of heating and the heating width produced by the device. These characteristics may be determined in the same manner as the write pole related characteristics discussed above, where heat as opposed to a magnetic field is used. As illustrated in FIG. 2, the axial zero field splitting parameter D(T) of an NV center is temperature dependent. With increasing temperature the energy gap between the $m_s=0$ and $m_s=-1$, +1 spin states is reduced and consequently the ESR frequency is shifted to lower values. FIG. 11A, by way of example, illustrates the temperature dependence of the ESR frequency with respect to temperature and FIG. 11B illustrates resulting resonance lines at different temperatures, e.g., 300° K and 700° K. Thus, by employing ODMR, the NV center may be used to measure local temperatures on the recording head with high spatial resolution, and thus, is suitable to characterize, e.g., near-field power at a near field transducer of a HAMR write head.

Figure 12:
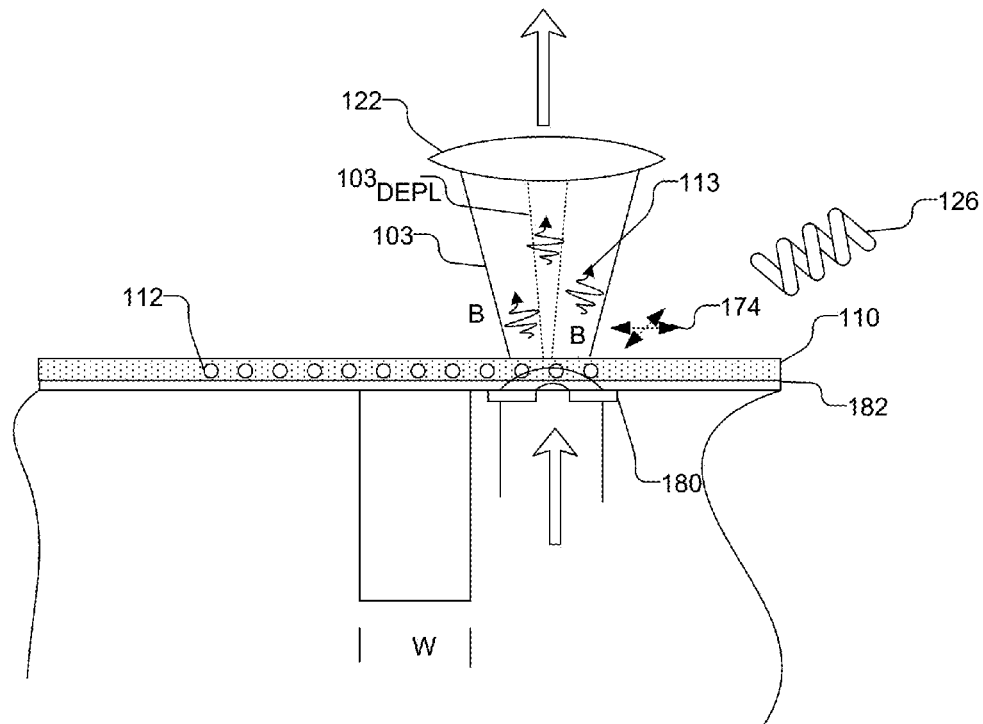
FIG. 12 schematically illustrates a diamond film with a plurality of nitrogen vacancy centers that is positioned to measure a near-field transducers of a Heat Assisted Magnetic Recording write head.

FIG. 12, by way of example, schematically illustrates the measurement of ODMR from a diamond film 110 with NV centers 112, similar to FIG. 9, with the diamond film 110 in contact with ABS of the recording head 114 having a near field transducer 180, e.g., used with a HAMR write head. In heat assisted magnetic recording (HAMR), the recording medium is locally heated by a near-field emanating from the near field transducer with, e.g. d=30 nm width. The recording head that is used in HAMR includes both a write pole and a thermal device, e.g., laser light source, that illuminates a near-field transducer 180 and by exiting plasmon resonance in the near-field, the near-field emanates from the transducer heating the recording medium. As discussed above in reference to FIG. 1, the thermal device of the recording head 114 instead of or in addition to the write pole may be controlled via the probe card 132 and the biasing source 131. The biasing source 131 used to control the thermal device may be, e.g., pulsed or DC and may be a constant or varying magnitude. If desired, separate probe cards and/or biasing sources may be used to control the write pole and thermal device. For example, multiple probes from a single probe card 132 may be connected to multiple biasing sources in order to separately engage either the write or the HAMR thermal device, or both, in situ, and either in sequential or simultaneous operation. If desired, the measurement may be performed using a diamond film 110 with the NV center 112 held on the tip of an Atomic Force Microscope (AFM) arm 176, as illustrated in FIG. 10.

Figure 13:
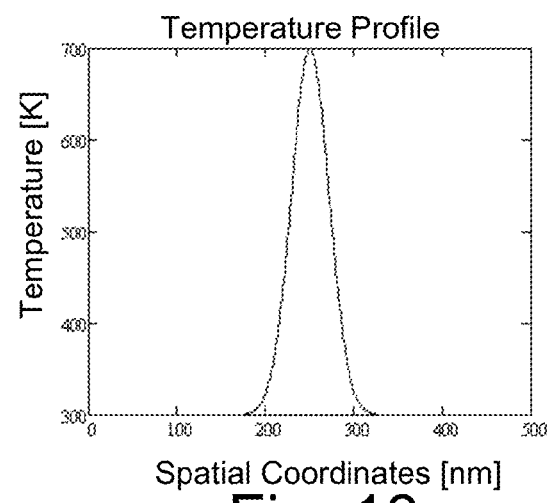
FIG. 13 illustrates the temperature profile produced by a near field transducer used in a Heat Assisted Magnetic Recording write head.

FIG. 13 illustrates the temperature profile produced by a near field transducer used in a HAMR write head. The NV centers 112 in the diamond film 110 may be used to measure the power of the near field at the transducer and/or the spatial extent of the transducer 180 in the same manner as the magnetic field and/or spatial extent of the write pole is measured. The diamond film 110 may be coated with a thin heat absorption layer 182, e.g., a few nanometers thick, that has low thermal conductivity, e.g. $SiO_2$, that functions as the recording medium to be heated. The diamond film 110 may be held close to or in contact with the ABS of the recording head 114. Moreover, the diamond film 110 may be deposited on the ABS of the recording head 114. Further, if desired, the diamond film 110 may be on the tip of an AFM arm as discussed above. The diamond film 110 may be, e.g., implanted with the NV centers 112 or may be a film that is embedded with nano-diamonds having NV centers. The diamond film 110 may be a mono crystalline diamond film with a matrix of equally spaced NV centers to measure the spatial extent of the near field transducer 180 and its power. The diamond film 110 may be a mono crystalline diamond film with a random distribution of NV centers 112 to measure the heating power with an estimate of the spatial extent of the near field transducer 180. If the diamond film 110 is a film with suspended nano-diamonds having a random distribution, the heating power of the near field transducer 180 may be measured.

As illustrated in FIG. 12, the recording head 114, including the transducer 180, is brought into contact with or sufficiently near the heat absorption layer 182 on the diamond film 110 that the near-field emanating from the transducer 180 locally increases the temperature of the heat absorption layer 182. The increase in temperature $\Delta T$ affects the electronic state of the NV centers 112 in the diamond film 110. An example of a temperature profile across the near field transducer is depicted in FIG. 13. As can be seen, the maximum heating occurs in the center of the spatial extent of the near-field transducer.

Figure 14:
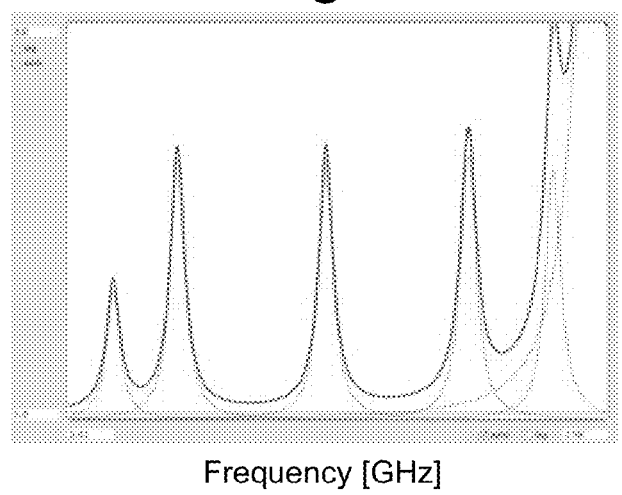
FIG. 14 is an ESR spectrum that may be generated while measuring a near field transducer and that may be evaluated to extract temperature information.
Figure 15:
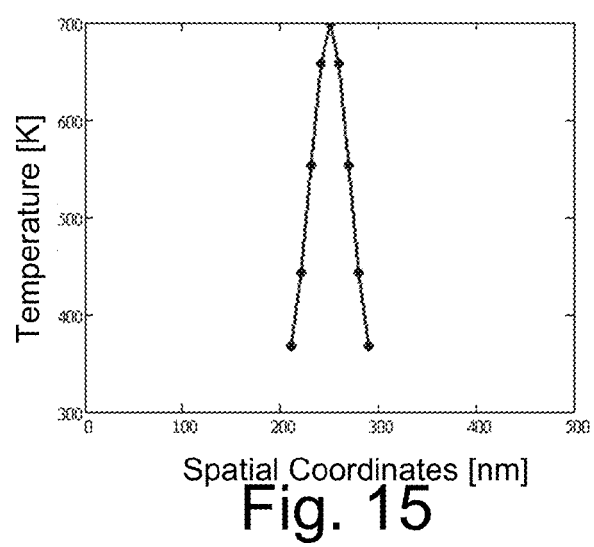
FIG. 15 illustrates a temperature profile extracted from an ESR spectrum.

As discussed above, a light source 102 (shown in FIG. 1) produces excitation illumination 103 that is incident on the diamond film 110 while in an external RF excitation field with varying excitation frequencies or pulse sequence produced by the RF antenna 126. In response to the excitation illumination 103 and while the near-field is produced by transducer 180, the NV center produces spin dependent PL 113 that is collected by the objective lens 122 and provided to the detector 130 (shown in FIG. 1). If desired, depletion illumination $103_{DEPL}$ may be scanned with respect to the recording head in two dimensions to measure ODMR. Moreover, as discussed above, a diamond film 110 with the NV center 112 held on the tip of an Atomic Force Microscope (AFM) arm 176, as discussed, in FIG. 10 may be used in place of the depletion illumination. The integral PL emitted by the NVs is collected with a high numerical aperture objective lens 122 while applying an RF-field of varying frequency or a pulse sequence. A magnetic field may be produced by the write pole or an external magnetic field source, or no magnetic field may be used. Using a matrix of equally spaced NV centers, a frequency spectrum of the ODMR signal, such as that illustrated in FIG. 14, may be generated and may be evaluated to extract temperature information, as illustrated in FIG. 15 in the same way as described for the write-field measurement, and using the known Temperature/ESR dependence, e.g., illustrated in FIGS. 11A and 11B. As can be seen in FIGS. 11A and 11B, temperature is inversely related to the ESR frequency, and thus, the minimum excitation frequency in the ESR spectrum is used to determine the maximum temperature. Additionally, because the maximum heating occurs at the center of the near-field transducer, the number of spectral lines in the ESR spectrum that are associated with the center of the near-field transducer may be used to determine the spatial extent of the near-field transducer. Moreover, if desired, the heat produced by the thermal device may be varied, e.g., by varying the applied bias signal to the thermal device, while producing a constant excitation frequency from the RF antenna 126. For example, the excitation frequency of the RF antenna 126 may be set at a level at which a known good thermal device in a recording head heats an absorption layer 182 to a specific temperature, and sample recording heads may be tested at that excitation frequency to determine the bias signal necessary to produce same temperature. Thus, the efficiency of the thermal device in the recording head may be determined.

Figure 16:
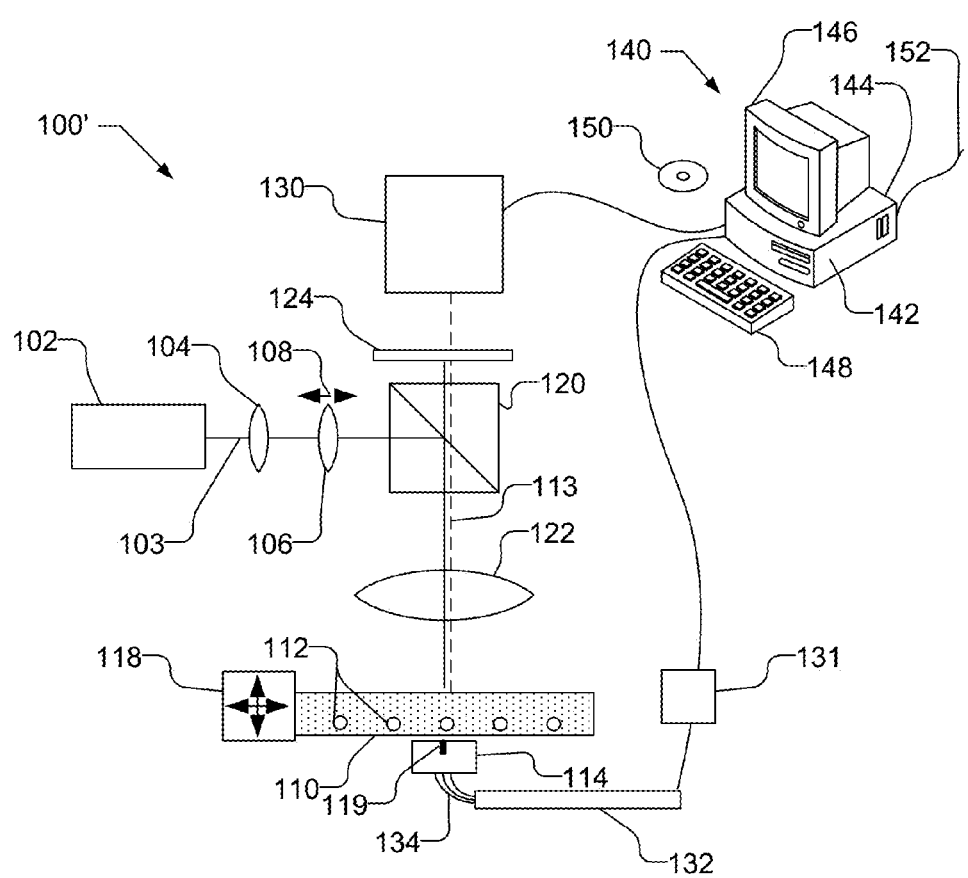
FIG. 16 illustrates an optical metrology device capable of characterizing a photon emitter on a nanometer length scale using photoluminescence (PL) produced by a substitutional impurity in a crystal film.

FIG. 16 illustrates an optical metrology device 100', similar to optical metrology device 100 shown in FIG. 1, like designated elements being the same, and is capable of characterizing a photon emitter on a nanometer length scale using photoluminescence (PL) produced by a substitutional impurity 112 in a crystal film 110. As optical metrology device 100' characterizes a photon emitter, there is no need for the radio wave frequency (RF) antenna 126, shown in FIG. 1. As discussed above, one or more nitrogen vacancy centers (NV centers) in a diamond crystal may be used. The NV centers, which are basically artificial atoms with distinct quantum energy levels, show unique extrinsic and intrinsic optical spin dynamics including stable photoluminescence based on radiating transitions between optically excited energy levels of their charged quantum states. The photoluminescence may be produced by the NV centers in response to excitation illumination. Additionally, the photoluminescence of an NV center may be turned "off" or reduced by the light emitted from a photon emitter that is under test due to a mechanism known as Stimulated Emission Depletion (STED) or alternatively by Ground State Depletion (GSD) or Charge State Depletion (CSD). STED is used in super-resolution (SRM) microscopy to achieve spatial resolution beyond the optical diffraction limit using a laser light source for photoluminescence depletion. Other than in SRM as discussed below, the STED light source in the present disclosure is the device under test. The optical metrology device 100' may optically detect the photoluminescence of one or more NV centers 112 in a crystal film 110, e.g. using photon counting by employing a photo detector on a scanning microscope or by using a camera with high sensitivity. By comparing the detected photoluminescence intensity produced in response to the excitation illumination when no STED illumination from the photon emitter under test is present and the detected photoluminescence intensity produced in response to the excitation illumination in the presence of STED illumination from the photon emitter, the quenching of the photoluminescence intensity may be determined, sometimes referred to herein simply as photoluminescence quenching. The characteristics of the photon emitter, including spatial and power characteristics, may be determined by analyzing the amount of photoluminescence quenching, e.g., by fitting the photoluminescence quenching to a model or comparing the photoluminescence quenching to a library of predetermined data.

The use of a confocal detection system enables detection of photoluminescence produced in response to the excitation illumination from only a small volume of the crystal film 110, e.g., 1 $\mu m^3$. The light source 102 may be, e.g., a laser, LED, etc., that excites the NV center with a continuous (CW) or pulsed excitation illumination, with one or more wavelengths in a range of 460 nm to 580 nm, and which may be, e.g., 532 nm. With pulsed excitation illumination, the pulse width may be, e.g., approximately 800 ps with a 4-MHz repetition rate. The light source 102 may have a power density of, e.g., 40 kW/cm$^2$, to polarize the NV center by pumping it between the ground and the excited levels. The light from the light source 102 may be provided to a collimator consisting of lenses 104 and 106 either directly or by way of an intervening optical element, e.g., fiber optics or a light pipe. The collimator 104, 106 expands and collimates the light, which is focused by lens 122, which is also used to collect the photoluminescence emanating from the NV centers. In an embodiment in which the device is a confocal microscope, the lens 106 (and/or other appropriate lens(es)) may be moved back and forth, as illustrated by arrow 108 and/or a 2-dimensional steering-mirror system could be used to move the excitation illumination 103 in the back-aperture plane of the objective lens 122 scanning the focused excitation illumination 103 in the sample plane. Additionally, appropriate apertures may be used in an embodiment in which the microscope is a confocal microscope. Moreover, if desired and as discussed below, additional light sources may be used along with light source 102.

A beam splitter 120 receives the excitation illumination from the light source 102 and provides at least a portion of the excitation illumination to the objective lens 122. The excitation illumination is focused on the surface of the crystal film 110 by the objective lens 122, which may have a high numerical aperture (NA=0.95) or an oil-immersion lens with an NA of, e.g. 1.3. The objective lens 122 may focus the excitation illumination on the crystal film 110 at a normal angle of incidence. It should be understood, however, that an oblique angle of incidence of the excitation illumination may be used if desired. The objective lens 122 focuses the light onto the crystal film 110 with one or more NV centers 112. The crystal film 110 and NV centers 112 are positioned to be in a near field emission of the photon emitter 119 under test. By way of example, FIG. 16 illustrates the photon emitter 119 as a part of a Heat Assisted Magnetic Recording (HAMR) recording head 114. The photon emitter 119, for example, may be a thermal device that heats the recording medium using a laser light source and a near field transducer. It should be understood, however, that the photon emitter 119 under test may be any other type of device that produces a near field of illumination. In addition to near field emitters, the optical metrology device may be used for characterization of far field photon emitters with nanometer precision, which may be useful for characterizing a laser, e.g., the beam waist of a focused laser, or optical fibers. For example, a focal spot of a focused laser beam may be as small as 200 nm in diameter, which cannot easily be characterized by conventional methods. By scanning the focal spot from a focused laser beam over the NV centers 112 or an optical fiber on the crystal film 110, for example, the profile of the laser beam or optical fiber may be resolved with nanometer resolution.

Figure 17A:
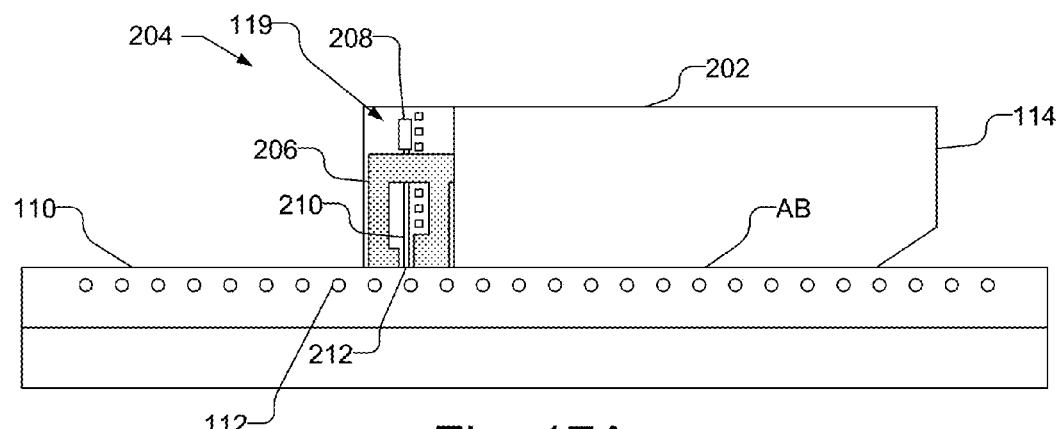
FIGS. 17A and 17B, by way of example, illustrate a side view and a back view, respectively, of recording head in contact with a crystal film.
Figure 17B:
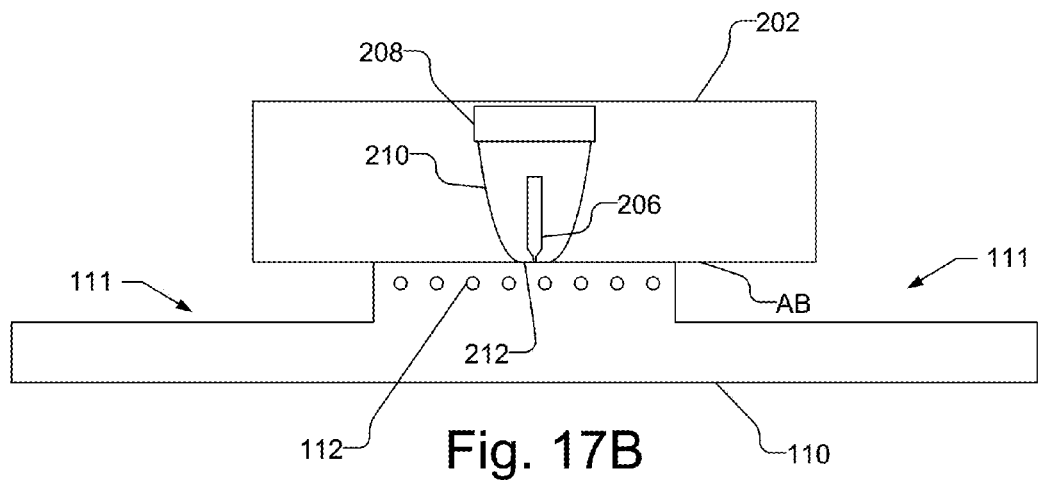

The crystal film 110 may be placed near or in contact with the photon emitter 119, or if desired, deposited on the air bearing surface (ABS) of the recording head 114, e.g., if the photon emitter 119 is part of the recording head. FIGS. 17A and 17B, by way of example, illustrate a side view and a back view, respectively, of recording head 114 in contact with crystal film 110. As illustrated in FIG. 17A, the recording head 114 includes a body, referred to as a slider 202, with a write pole structure 204, illustrated greatly enlarged, coupled to the back end of the slider 202. A light source 208, e.g. a laser diode, that is near the write pole structure 204 including the write pole 206 is integrated into the recording head 114. Light from the integrated light source 208 is coupled to a near field transducer 212 at the ABS via an optical wave guide 210. The near field illumination is produced by the near field transducer 212 at the air bearing surface AB. As can be seen in FIG. 17B, the top surface of the crystal film 110 may be patterned, illustrated with notches 111, forming islands with a width that is greater than a maximum dimension of the expected quenching profile, i.e., the area subject to photoluminescence quenching by STED near field illumination produced by the photon emitter 119. For example, the island width may be approximately half the width of the slider 202 or less. The length of the island is optional and may be greater than the length of the slider 202, and, in fact, may extend the length of the crystal film 110 if desired. The ABS of the recording head 114, and more particularly, the near field transducer 212, may be placed in contact with the crystal film 110 on a patterned island of the crystal film 110.

The NV centers 112 in the crystal film 110 may be arranged in the form of a matrix and may have a uniform or a random distribution with a defined average density. Different average densities of the NV centers 112 in the crystal film 110 may be used depending on how the optical metrology device 100' collects the photoluminescence. By way of example, however, an average density of the NV centers 112 may be, e.g. 200 NV centers per μm$^2$ or such that the distance between adjacent NV centers 112 is similar to or less than the dimension of the expected quenching profile, i.e., the area subject to photoluminescence quenching. Alternatively, the crystal film 110 may, in fact, include a number of small crystals, each containing a number of NV centers 112. If desired, optical metrology device 100' may include additional optic elements to move the excitation illumination over the crystal film 110, e.g., in one or two dimensions. In one embodiment, as discussed below, a second light source may be provided that produces STED illumination with a ring shaped beam that has a central zero intensity at the focal plane that is coincident with the excitation illumination and which is scanned over the crystal film 110. Alternatively, a single (or few) NV center 112 may be used in the crystal film 110. In such an embodiment, relative movement between the recording head 114 and the crystal film 110 may be produced, e.g., as illustrated by actuator 118 in FIG. 16.

During measurement, photoluminescence 113 produced by the NV centers 112, illustrated by the dotted line, will be collected by the objective lens 122 and directed by the beam splitter 120 towards a detector 130. As illustrated, a spectral filter 124, such as a dichroic film, is positioned before the detector 130 to remove any reflected excitation illumination and STED illumination from the photon emitter 119 and to direct only the photoluminescence to the detector 130. The spectral filter 124, thus, may be a long-pass filter with a wavelength cut-off at, e.g., 580 nm, or a narrow band pass filter with a center wave length of e.g. 637 nm, to filter out any remaining excitation illumination and STED illumination. The detector 130 may be, e.g., a non-imaging photodetector, such as a silicon avalanche photodiode operating in the signal photon counting regime, which detects the optical intensity at a single spot. Alternatively a CCD camera can be used to detect the intensity of the photoluminescence.

The detector 130 is connected to a computer 140 and the computer 140 receives, stores, and analyzes the optically detected data provided by the detector 130. The computer 140 includes a processor 142 with memory 144, as well as a user interface including e.g., a display 146 and input devices 148. A non-transitory computer-usable storage medium 150 having computer-readable program code embodied may be used by the computer 140 for causing the processor 142 to control the optical metrology device 100' and to perform the functions including the analysis described herein. The data structures and software code for automatically implementing one or more acts described in this detailed description can be implemented by one of ordinary skill in the art in light of the present disclosure and stored, e.g., on a computer readable storage medium 150, which may be any device or medium that can store code and/or data for use by a computer system such as processor 142. The computer-usable storage medium 150 may be, but is not limited to, magnetic and optical storage devices such as disk drives, magnetic tape, compact discs, and DVDs (digital versatile discs or digital video discs). A communication port 152 may also be used to receive instructions that are used to program the computer 140 to perform any one or more of the functions described herein and may represent any type of communication connection, such as to the internet or any other computer network. Additionally, the functions described herein may be stored in memory 144 or embodied in whole or in part within the circuitry of an application specific integrated circuit (ASIC) or a programmable logic device (PLD), and the functions may be embodied in a computer understandable descriptor language which may be used to create an ASIC or PLD that operates as herein described.

As illustrated, the computer 140 may be coupled to the recording head 114, via a probe card 132 which is connected to the recording head 114 using one or more probes 134, which may be, e.g., pogopins, probes, or other contacts such as wires that are wire bonded. The probe card 132 may be coupled to a biasing source 131 that provides a bias signal, such as a current or voltage signal, which is provided to the recording head 114 via the probe card 132 and controls the photon emitter 119, i.e., a high intensity light source, on the recording head 114. If the light source is separate from the recording head 114, e.g., the probe card 132 may control the light source, which is remote from the recording head 114, to produce illumination that is incident on the photon emitter 119, which operates as a near field transducer.

The biasing source 131 may be connected to and controlled by the computer 140. The computer 140, thus, may control the illumination produced by the photon emitter 119 on the recording head 114, e.g., by controlling the bias signal provided to the recording head (or separate illumination source). The biasing source 131 may provide a plurality of bias signals with different levels to the recording head 114. Accordingly, the recording head 114 may be controlled via the biasing source 131 to produce near field illumination with a desired intensity that is constant or varying with a desired pulse width and frequency. The varying near field illumination produced by the photon emitter 119 may vary continuously or in a stepped manner.

Accordingly, the recording head 114 may be controlled via the biasing source 131 to produce a constant or varying near field illumination. Additionally, when the recording head 114 includes a Dynamic-Flying Height (DFH) device, one of the probes 134 of the probe card 132 may be used to provide current to the microactuator device from a second circuit in the current or voltage source that is connected to the computer 140. Write heads use a DFH device as an adjustment mechanism to internally bias the write pole structure, including the photon emitter, closer to or further from the air bearing surface. The DFH device is typically in the form of a heater incorporated into the write head structure, with additional contact pads for external connection. By applying a bias to the additional contact pads via the probe card 132, the position of the photon emitter 114 can be adjusted towards or away from the air bearing surface of the write head. By adjusting the position of the photon emitter 119 via the DFH device, the performance of the photon emitter 119 may be measured at different vertical displacement from the crystal film 110.

Additionally, when the recording head 114 includes a microactuator device, one of the probes 134 of the probe card 132 may be used to provide current to the microactuator device. The source of the current may be a second circuit in the current or voltage source connected to the computer 140. Write heads use a microactuator device as an adjustment mechanism to move the write pole structure, including the photon emitter, in the cross-track direction to better align the write pole structure to the lands of a disk that is being written to. The microactuator device is incorporated into the write head structure, which includes additional contact pads for external connection. By applying a bias to the additional contact pads via the probe card 132, the position of the photon emitter 119 can be adjusted in the cross-track direction. By adjusting the position of the photon emitter 119 via the microactuator device during measurement with the device, the performance of the microactuator may be verified and the characteristics of the photon emitter 119 may be measured at different positions. Additionally, with an adequate density of NV centers, e.g., a low NV center density, and sufficient movement caused by the microactuator device, the microactuator device may be used to produce relative movement between the crystal film 110 and the photon emitter 119 during measurement.

As discussed above, the crystal film 110 contains one or more substitutional impurities 112, such as NV centers. An NV center in diamond is a naturally occurring or technically created impurity in, e.g., a diamond crystal where a Nitrogen atom replaces a Carbon atom creating a vacancy next to the Nitrogen atom. Nitrogen vacancy centers may be created in a diamond crystal, e.g., using a type-Ib HPHT single-crystal sample that is initially embedded with nitrogen impurities. For example, nitrogen impurities may be embedded by irradiation with a an ion-beam, e.g. $N_2^+$ ions at 5 keV, in case of a very high purity diamond film or by an electron beam in case the diamond film already has nitrogen impurities and annealing, e.g., for 2 hours at 850° C. The density of the NV centers within the crystal film may be controlled, e.g., by controlling the applied irradiation dose, or using appropriate masking techniques. For example, an ion beam fluence of $10^{11}$ cm$^2$ can result in a density of $8 \times 10^{10}$ NV cm$^{-2}$. Moreover, by controlling the energy of the implantation as well as the annealing process the depth of the NV centers implanted in the crystal may be controlled.

An NV center may be optically excited, e.g., with excitation illumination having a wavelength range from 460 nm to 580 nm, which yields an intense photoluminescence emission from the NV center with lifetimes in the millisecond range. For example, the NV center may be excited with a laser at a wavelength of 532 nm and in response will emit a broadband luminescence with a zero phonon line at 637 nm, at room temperature. In the mechanism of stimulated emission, an electron in an excited state gives energy to an incoming photon and is forced to the ground state before it can create photoluminescence by spontaneous emission.

In addition, the photoluminescence of an NV center may be turned "off" or the intensity reduced in time when the pulse of excitation illumination is followed by a longer wavelength, or with the same wavelength, pulse of sufficient intensity, e.g., from the photon emitter 119 under test, due to a mechanism known as Stimulated Emission Depletion (STED). By way of example, the excitation illumination may have a wavelength of 532 nm and a duration of 60 ps followed by a longer wavelength pulse from the photon emitter 119 under test, e.g. 830 nm, with a duration 3.2 ns, of sufficient intensity to quench the intensity of the photoluminescence. If desired, STED with a continuous (CW) or quasi CW illumination may be employed.

Thus, one or more NV centers in a crystal film may be used to measure characteristics of the photon emitter, including spatial and power characteristics by detecting quenching of the photoluminescence intensity produced by NV centers caused by the near field illumination of the photon emitter. The photoluminescence quenching data may be analyzed, e.g., by fitting to a model or comparing a library of data, to determine the desired characteristics of the photon emitter.

Figure 18:
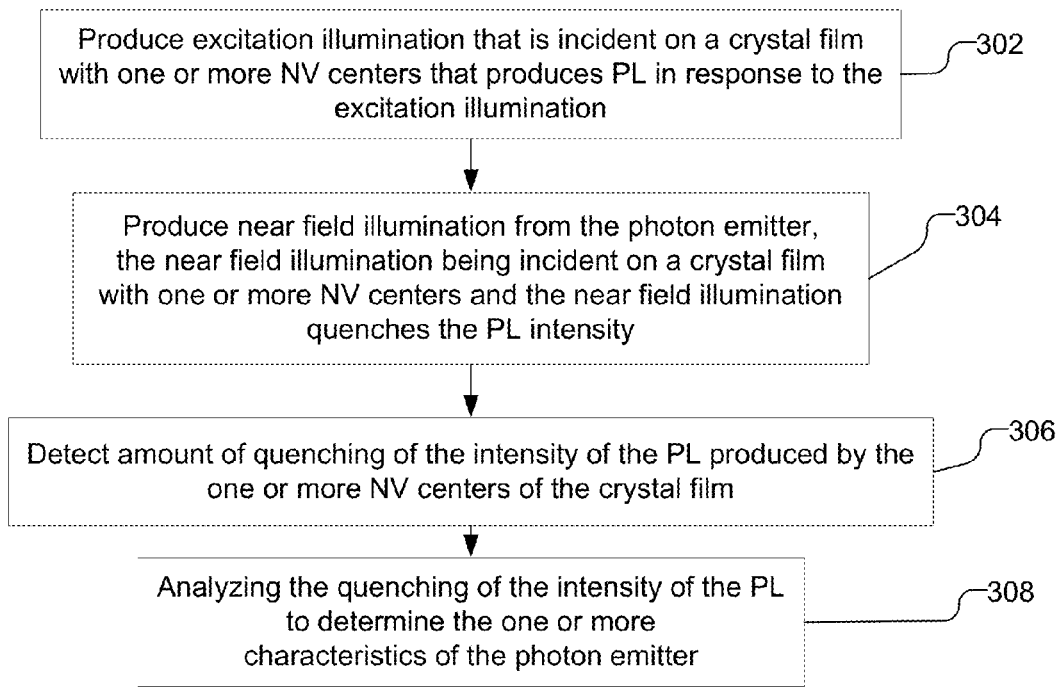
FIG. 18 is a flow chart illustrating a method of determining one or more characteristics of a photon emitter using NV centers and an optical metrology device.

FIG. 18, by way of example, is a flow chart illustrating a method of determining one or more characteristics of a photon emitter using NV centers and an optical metrology device, such as the optical metrology device 100'. As illustrated, excitation illumination is produced, e.g., by the optical metrology device 100', and is incident on a crystal film with the one or more NV centers (302). As discussed above, the NV centers produce photoluminescence having an intensity in response to the excitation illumination. Illumination is produced from the photon emitter, where the illumination is incident on the crystal film with the one or more NV centers (304). The illumination produced by the photon emitter quenches the intensity of the photoluminescence from the one or more nitrogen vacancy centers. The illumination from the photon emitter may be near field illumination or far field illumination. For example, the illumination may be produced by providing a bias signal to the photon emitter, which causes the photon emitter to generate near field illumination. Where the photon emitter is a laser diode, a bias current may be used, but a bias voltage may be used for other types of light sources if appropriate. For example, if the photon emitter may include a laser light source and near field transducer on a recording head, the bias current may be provided to the recording head via the probe card 132 to cause the photon emitter to emit the near field illumination. Alternatively, the light source may be remote from the photon emitter, e.g., as illustrated with the near field transducer 114 in FIG. 17A, where light from the remote light source is provided to the near field transducer, which produces the near field illumination in response. The illumination may be far field illumination, such as that produced by a laser or fiber optics.

The amount of quenching of the intensity of the photoluminescence produced by the one or more NV centers caused by the illumination of the photon emitter is detected (306). The amount of quenching of the intensity of the photoluminescence may be detected by subtracting the background photoluminescence intensity. In other words, a first photoluminescence intensity may be detected from the one or more NV centers in response to the excitation illumination without the presence of the illumination produced by the photon emitter. A second photoluminescence intensity may be detected from the one or more NV centers in response to the excitation illumination in the presence of the illumination produced by the photon emitter, i.e., while the illumination from the photon emitter quenches the intensity of the photoluminescence from the NV centers. The amount of quenching of the intensity of the photoluminescence may then be determined based on a difference between the first photoluminescence intensity and the second photoluminescence intensity.

The amount of quenching of the intensity of the photoluminescence is analyzed to determine the one or more characteristics of the photon emitter (308). For example, the amount of quenching of the intensity of the photoluminescence may be analyzed by fitting the detected amount of quenching of the intensity of the photoluminescence to a photoluminescence quenching model. By way of example, the detected amount of photoluminescence quenching may be used in a non-linear, multi parameter fit to a model of a photoluminescence quenching distribution profile to determine the desired characteristics of the photon emitter. Additionally, or alternative, the amount of quenching of the intensity of the photoluminescence may be analyzed by comparing the amount of quenching of the intensity of the photoluminescence to a library of data, which is pre-generated and stored, e.g., in memory of the metrology device. The pre-generated data in the library may be produced, e.g., using the photoluminescence quenching model or in any other desired manner, such as empirically. The amount of quenching of the intensity of the photoluminescence may be analyzed in other manners as will be evident to those of ordinary skill in the art in light of the present disclosure. Characteristics that may be determined by analyzing the amount of quenching of the intensity of the photoluminescence, for example, may be the peak power or a width of the distribution profile. The width of the profile, for example when using a Lorentzian, may be the Full Width Half Magnitude (FWHM) or FWHM Half Magnitude (HWHM) or other equivalent measure, but for the sake of ease of reference will be referred to herein as FWHM. The characteristics of the photon emitter may be determined for different bias currents provided to the photon emitter. Moreover, the quenching data may be detected as a function of the bias current provided to the photon emitter and analyzed, e.g., by fitting to a photoluminescence quenching model of an integrated photoluminescence quenching profile or comparing to a library of data to determine characteristics such as the width of the distribution profile and a power scaling factor. Again, the library of data may be produced, e.g., using the photoluminescence quenching model of an integrated photoluminescence quenching profile or in any other desired manner, such as empirically.

Figure 19:
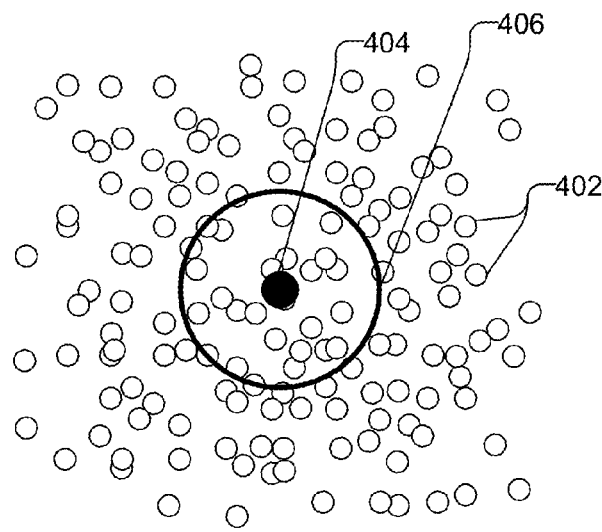
FIG. 19, by way of illustration, shows a portion of a crystal film with a plurality of luminescing NV centers, illustrated as white spots.

FIG. 19, by way of illustration, shows a portion of a crystal film with a plurality of luminescing NV centers 402, illustrated as white spots, only a couple of which are labeled 402. As can be seen, the distribution of NV centers 402 may be inhomogeneous, i.e., non-uniform, but a crystal film with a homogeneous, i.e., uniform, distribution of NV centers may be used if desired. The crystal film, by way of example, may be a single crystal with a number of NV centers or a plurality of nano-crystals combined into the film, each nano-crystal containing one or more NV centers. The NV centers are in the same x/y plane and may have a defined average density, e.g., of 200 NV centers per square micron, or an average spacing of 60 nm±30 nm, but other average densities and/or average spacing may be used depending on the physical characteristics of the photon emitter under test. The spatial resolution is determined by the distance between the near-field illumination and the NV centers. Accordingly, for nanometer scale resolution, the NV centers should be relatively close to the top surface of the crystal film, e.g., a distance of 5 nm or less.

As discussed above, the NV centers are excited with excitation illumination at a wavelength of 532 nm, and luminesce at 637 nm, which may be collected, e.g., using a wide-field microscope with a CCD camera or a scanning microscope with a photodetector. The illumination from the photon emitter, however, will quench, i.e., turn off or reduce the intensity photoluminescence of the NV centers, due to STED. FIG. 19 illustrates a photon emitter 404 under test as a spot and further illustrates a diffraction limited spot 406 of the imaging system as a reference. By way of example, the photon emitter 404 may have a wavelength of, e.g., 700 nm to 900 nm and may be a continuous wave (CW) or pulsed light emitter.

Figure 20:
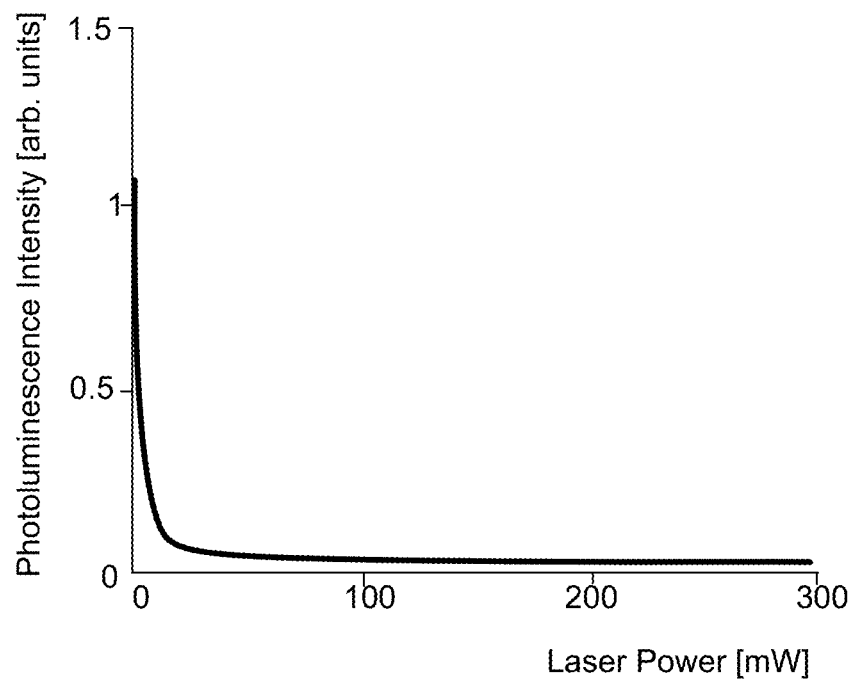
FIG. 20 illustrates the quenching of the photoluminescence intensity produced by the NV centers caused by a near-infrared CW laser beam.

The crystal film with NV centers has a characteristic dependence of STED on the power of the quenching light source. FIG. 20, by way of example, illustrates the quenching of the photoluminescence intensity produced by the NV centers, i.e., the background subtracted photoluminescence intensity, caused by a near-infrared CW laser beam, where the y-axis represents photoluminescence intensity in arbitrary units, and the x-axis represents the laser power of the quenching light source in mW. The photoluminescence quenching dependence DP is described by an exponential function as follows:

$$DP(I) = m(I - I_0)^n + \text{const} \qquad \text{eq. 1}$$

where "I" represents the general intensity, which may be uniform or locally varying, of the quenching light source, m is the quenching scaling factor and n the quenching exponent, and const is the asymptotic depletion value for very high depletion light intensity, for example, at 300 mW illustrated in FIG. 20. The power dependence of the crystal film has to be measured once to determine the parameters $I_0$, m, n and const. The calibration of the power dependence of the crystal film may be performed using an external laser light source, e.g., laser, with known intensity I to produce data such as that shown in FIG. 20. Preferably, the calibration of the power dependence of the crystal film is performed at the location on the crystal film that will be used to test photon emitters, but if the average density of NV centers is uniform over the entire crystal film, calibration of the power dependence of the crystal film may be performed anywhere on the crystal film.

Figure 21:
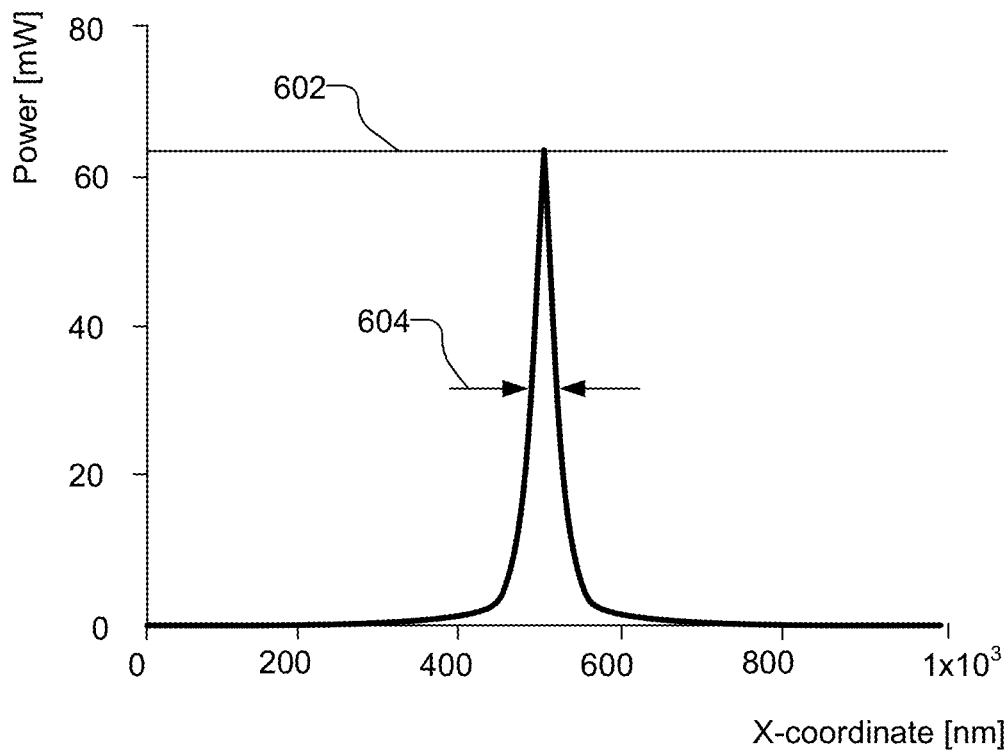
FIG. 21 illustrates a near field illumination profile for a near field photon emitter.

The photon emitter may be characterized based on its peak power and its spatial distribution. FIG. 21, by way of example, illustrates a near field illumination profile for a near field photon emitter, where the y-axis represents power of the photon emitter in mW and the x-axis represents the x-coordinate in nm. The peak power of the near field illumination profile is illustrated by line 602 and the FWHM is illustrated by arrows 604. The near field illumination profile NF is described by a Lorentzian function with a parameter w that is the FWHM of the near-field distribution determined by the aperture size and the peak power (P) of the photon emitter as follows:

$$NF(x, y, P) = P \frac{w^2}{4[(x-x_0)^2 + (y-y_0)^2] + w^2} \qquad \text{eq. 2}$$

where $x_o$ and $y_0$ are the coordinates with the peak power P. A Lorentzian function is used in a model as an example but this could also be a Gaussian or any other function that can describe the near-field distribution. The use of different model functions may yield different or additional characteristic parameters of the photon source related to the extent and geometry of the near-filed distribution.

Figure 22:
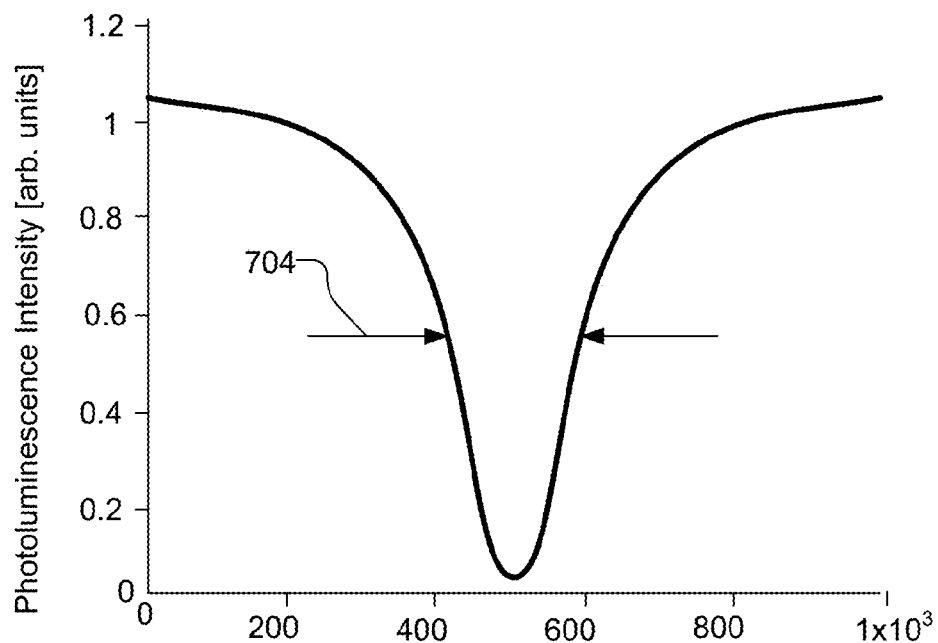
FIG. 22 illustrates an example of a photoluminescence quenching profile for the NV centers of a crystal film.

FIG. 22 illustrates an example of a photoluminescence quenching profile for the NV centers of a crystal film, where the y-axis represents photoluminescence intensity in arbitrary units and the x-axis represents the x-coordinate in nm.

As can be seen with a comparison of FIGS. 6 and 7, the FWHM of the photoluminescence quenching profile (illustrated by arrows 704) may be larger than the FWHM of the near field illumination profile. The locally varying photoluminescence quenching $I_{STED}$ may be using equation 2 and equation 1 as follows:

$$I_{STED}(x,y,P) = DP(NF(x,y,P)) \qquad \text{eq. 3}$$

Substituting NF(x,y,P) in equation 2 for the intensity I in equation 1, results in the following:

$$I_{STED}(x, y) = m\left[P\frac{w^2}{4[(x-x_0)^2 + (y-y_0)^2] + w^2} - I_0\right]^n \qquad \text{eq. 4}$$

where $I_{STED}(x, y)$ is the locally varying amount of quenching of the intensity of the photoluminescence with const=0, and P and w are fitting parameters of the peak power and the FWHM of the near field illumination profile, respectively, for a rotationally symmetric distribution.

Figure 23:
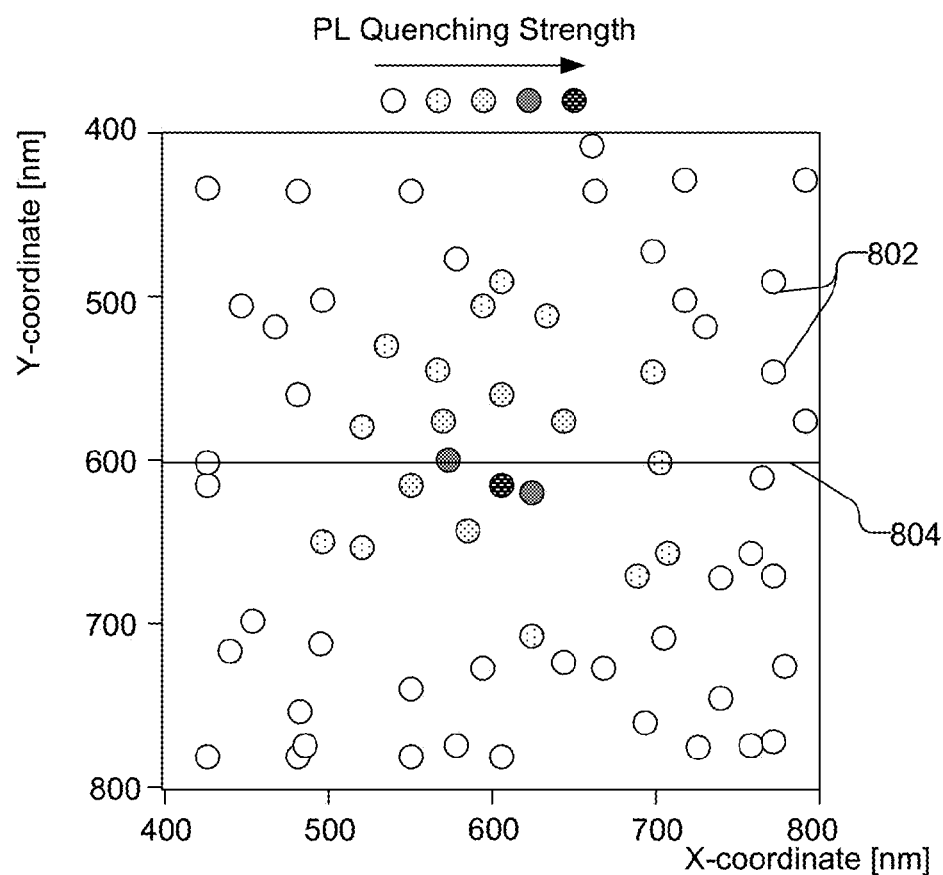
FIG. 23 shows in two dimensions the detected quenching of the intensity of the photoluminescence produced by the NV centers caused by near field illumination of a photon emitter.

FIG. 23, by way of illustration, shows in two dimensions the detected quenching of the intensity of the photoluminescence produced by the NV centers 802 caused by near field illumination of a photon emitter. In FIG. 23, the NV centers are illustrated as spots, with darker spots representing increased quenching. The near field illumination produced by the photon emitter interacts with the NV centers 802 turning off or reducing the intensity of the photoluminescence for individual NV centers when the near field illumination at the individual NV centers is greater than a characteristic threshold value. The photoluminescence quenching of FIG. 23 may be determined as the difference in the measured photoluminescence intensity from the NV centers without the quenching illumination from the photon emitter and the measured photoluminescence intensity from the NV centers in the presence of the quenching illumination from the photon emitter. The intensity of the photoluminescence from the NV centers may be measured using, e.g., a wide-field microscope with a CCD camera or a scanning microscope with a photodetector, which may be scanned in the x and y coordinates. Once the photoluminescence quenching is detected, it may be analyzed, e.g., by fitting to a photoluminescence quenching model or compared to a library of data, to determine the desired characteristics of the photon emitter.

Figure 24:
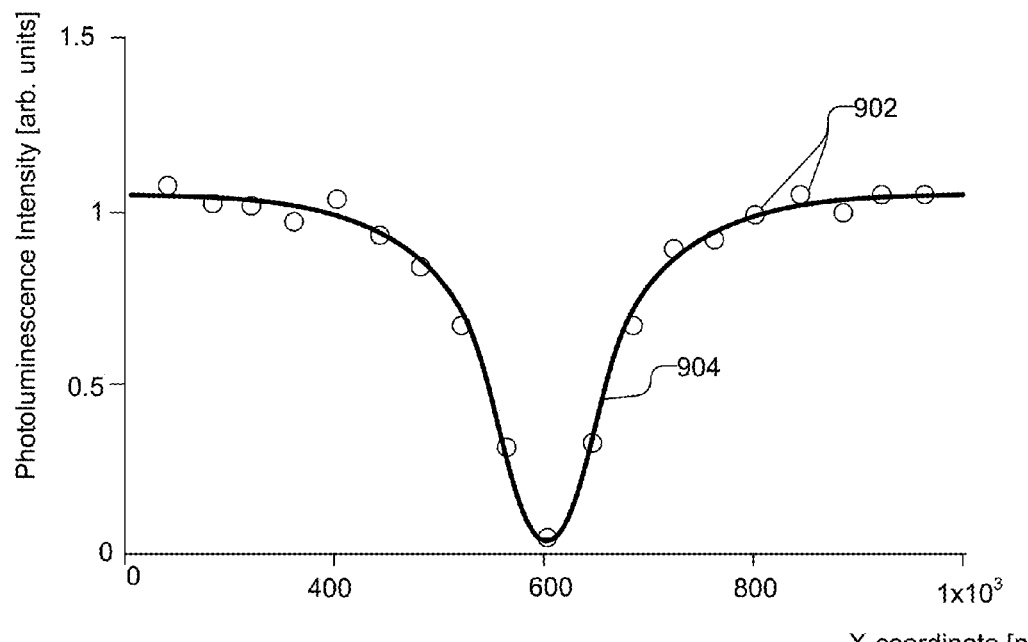
FIG. 24 shows detected photoluminescence quenching data along with a fit curve illustrating a spatially resolved quenching profile.

FIG. 24, by way of illustration, shows detected photoluminescence quenching data, i.e., the amount of quenching of the intensity of the photoluminescence from the NV centers, as spots 902, along with a fit curve 904 illustrating a spatially resolved quenching profile. The photoluminescence quenching data may be detected along a horizontal line 804 in FIG. 23. The center line 804 may be determined from a two-dimensional distribution of the photoluminescence quenching data as a line that extends through the point or area with the strongest quenching. The two-dimensional distribution of the photoluminescence quenching data may be produced from a two-dimensional scan of the photon emitter. Alternatively, a one-dimensional scan of the photon emitter may be used to produce the photoluminescence quenching data from the NV centers if the scan passes through the point or area with the strongest quenching. The detected photoluminescence quenching data may be analyzed, e.g., by fitting to a photoluminescence quenching model, such as equation 4, or compared to a library of data, which may be produced using the model or empirically, to determine the one or more characteristics of the photon emitter. Thus, for example, a non-linear, multi parameter fit to the photoluminescence quenching profile model may be used to determine the peak power P and the width of the near field illumination profile. For example, the parameter fit such as that illustrated in FIG. 24 may provide a FWHM of 29.03 nm and a peak power P of 3083 [a.u.] for the near field illumination profile.

Additionally, by varying the separation between the photon emitter and the NV centers, the decay of the near-field power in the z-direction may also be measured. The separation between the photon emitter and the NV centers may be controlled by moving the crystal film, e.g., using a Atomic Force Microscope (AFM) or other actuator holding the crystal film and/or by moving the photon emitter, e.g., using a dynamic fly height (DFH) adjustment on the recording head.

If desired, the photoluminescence quenching may be detected for varying bias currents that are applied to the photon emitter and the peak power and FWHM of the near field illumination profile may be determined for different bias currents.

Figure 25:
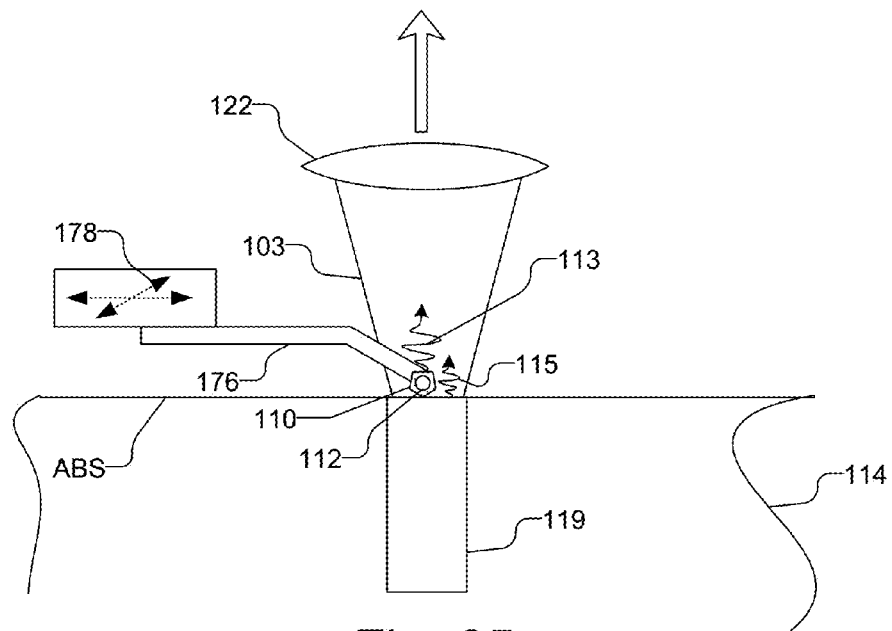
FIG. 25 schematically illustrates one implementation in which a crystal film with one or more NV centers is held on the tip of an Atomic Force Microscope (AFM) arm to measure a photon emitter.

The optical metrology device 100' shown in FIG. 16 may detect the quenching of the intensity of the photoluminescence caused by a near field photon emitter in various manners. For example, FIG. 25 schematically illustrates one implementation in which a crystal film 110 with one or more NV centers 112 is held on the tip of an Atomic Force Microscope (AFM) arm 176 to measure a photon emitter 119. The embodiment shown in FIG. 25 is similar to the embodiment shown in FIG. 10, without the RF antenna 126, like designated elements being the same. The crystal film 110 with one or more NV centers 112 on the tip of the arm 176 is in contact with or at a controlled distance from the photon emitter 119 on the recording head 114. The crystal film 110 may be a micron sized diamond particle that includes a single or several NV centers 112. The AFM arm 176 may be scanned over the photon emitter 119 on the recording head 114 in one or two dimensions, as illustrated by arrows 178. The use of a crystal film 110 with one or more NV centers 112 is held on the tip of an Atomic Force Microscope (AFM) arm 176 may be used in place, e.g., of the STED illumination embodiments discussed herein. As discussed above, a light source 102 (shown in FIG. 16) produces excitation illumination 103 that is focused by the objective lens 122 onto the crystal film 110. In response to the excitation illumination 103, the NV center 112 produces photoluminescence 113 that is collected by the objective lens 122 and provided to the detector 130 (shown in FIG. 16). As the crystal film 110 is scanned across the recording head 114, including the photon emitter 119 and ABS, at each measurement position, the intensity of the photoluminescence 113 is measured with and without the near field illumination 115 from the photon emitter 119 to detect the quenching of the intensity of the photoluminescence at each measuring position. With the photoluminescence quenching detected at a plurality of measuring positions, a one dimensional line profile or two-dimensional distribution of the photoluminescence quenching may be determined. With a two-dimensional distribution of the photoluminescence quenching, the line profile through the strongest quenching point may be used to derive the peak power or the width of the near field illumination profile of the photon emitter by analyzing the amount of quenching of the intensity of the photoluminescence, e.g., by fitting to a photoluminescence quenching model, or compared to a library of data, which may be produced using the model or empirically, as discussed above. If desired, the scan may be repeated for different values of the bias current supplied to the light source, or equivalently, different values of the bias current may be supplied to the light source at each position during a single scan of the crystal film 110.

Moreover, as discussed above, by varying the separation between the photon emitter and the NV centers, the decay of the near-field power in the z-direction may also be measured. The separation between the photon emitter and the NV centers may be controlled by moving the crystal film, e.g., using an actuator holding the crystal film and/or by moving the photon emitter, e.g., using a dynamic fly height (DFH) adjustment on the recording head. Further, the photoluminescence quenching may be detected for varying bias currents that are applied to the photon emitter and the peak power and width of the near field illumination profile may be determined for different bias currents.

In another implementation, the photoluminescence quenching of the intensity of the photoluminescence produced by a near field photon emitter may be detected without using relative movement between the photon emitter and the crystal film. For example, the optical metrology device may use scanning external STED illumination while the photon emitter and crystal film are held stationary with respect to each other.

FIG. 26 illustrates, by way of example, the optical metrology device 100' with additional light sources to produce STED illumination to improve resolution and to scan the photon emitter. The optical metrology device 100' in FIG. 26 is similar to the embodiment shown in FIG. 4, without the RF antenna 126, like designated elements being the same. As illustrated, optical metrology device 100' includes a second light source 102$_{STED}$ that produces STED illumination 103$_{STED}$ having a different wavelength as the light source 102, and that is coincident on the crystal film 110 with the excitation illumination 103 from light source 102. The light source 102 produces excitation illumination 103 that has a Gaussian point spread function and produces a relatively large diffraction limited spot on the crystal film 110. FIG. 27, by way of example, illustrates the Gaussian point spread function of the excitation illumination 103 with a solid line. The second light source 102$_{STED}$ produces light that passes through a vortex phase plate 164 to produce a ring shaped beam that has a central zero intensity at the focal plane. FIG. 27, by way of example, illustrates a ring shaped point intensity distribution of the STED illumination 103$_{STED}$, which is coincident with the excitation illumination 103. The STED illumination 103$_{STED}$ quenches the intensity of the photoluminescence produced by the NV centers 112 in the crystal film 110 that are off-center relative to the excitation illumination 103, so that the off-center NV centers only contribute a constant background, which may be subtracted from the photoluminescence quenching signal produced by the photon emitter 119 under test, thereby providing a photoluminescence quenching signal from only the NV centers in the center of the STED illumination 103$_{STED}$. FIG. 28 illustrates the effective point intensity distribution 166 of the excitation illumination 103 combined with the STED illumination 103$_{STED}$. The coincident excitation illumination 103 and STED illumination 103$_{STED}$ may be scanned over the crystal film 110 at the region of interest by two-dimensional deflection in the back aperture of the objective lens 122 to detect the photoluminescence quenching caused by the photon emitter 119 in two dimensions, e.g., using one or more mirrors 117 in the beam path, which may be controlled by the computer 140.

The STED illumination 103$_{STED}$ may have a wavelength greater than the excitation illumination 103, e.g., greater than 532 nm, and with increased power. For example, a reduction in the photoluminescence may be achieved for STED illumination $103_{STED}$ with power greater than 2 MW/cm$^2$. The STED illumination $103_{STED}$ may be continuous (CW) or pulsed excitation, with a pulse width of, e.g. 150 ps, where a pulsed STED illumination $103_{STED}$ results in stronger quenching of the intensity of the photoluminescence.

By determining the characteristics of the photon emitter, e.g., the peak power or power conversion factor and the aperture diameter determined, a finished photon emitter may be verified. For example, where the photon emitter is on a recording head, e.g., a HAMR head, each finished slider (or a sampling of finished sliders) may be verified by comparing the determined characteristics to an acceptable threshold. Recording heads with photon emitters having a peak power, a power conversion factor, or aperture diameter that is not within acceptable levels may be rejected.

Additionally, the characteristics of the photon emitter may be used in the process of attaching photon emitters to sliders, in the case of a HAMR head, or other types of devices. For example, the characteristics of the photon emitter, e.g., peak power, may be detected while actively aligning the laser light source to the slider, thereby enabling an optimum alignment between the laser light source and the slider, or other types of devices.

Additionally, the photon emitter discussed herein is a near field illumination source, such as the type used in recording heads. However, if desired, other near field illumination photon emitters may be tested, including optical fibers, plasmon tips for optical near field microscopy (SNOM), nano-photonics devices, optical wave-guides, laser-diodes, laser focal spot (beam waist) characterization. Moreover, it is possible to measure characteristics of far field emitters, such as a laser or fiber optics. For example, the process may be used to profile a laser beam produced by a laser or characterize fiber optics with a high degree of precision, i.e., on a nanometer length scale.

In another embodiment, a probe resembling, e.g., an Atomic Force Microscope (AFM) probe in shape and size and that is suitable to be attached to an AFM, may be created from a diamond film. The probe includes a tip that incorporates a single or a multitude of NV centers located near the end of the tip facing the device under test. A beveled portion at the end of the probe arm directs excitation light to the NV center and directs photoluminescence light emanating from the NV center into the probe arm. The probe arm acts as an optical waveguide to propagate the emission from the NV center with high efficiency. Various optical components may be mounted to the probe, e.g., via a beam splitter, including the light source (or a portion of the light source), a detector, as well as an RF antenna, if used. The integrated components enable excitation of photoluminescence in the NV center as well as optically detected Electron Spin Resonance (ODMR) and temperature measurements. Further, the probe may serve as a light probe utilizing the physical effect of Stimulated Emission Depletion (STED) caused by light from the light source under test acting on the photoluminescence radiation emanating from the NV center.

Figure 29:
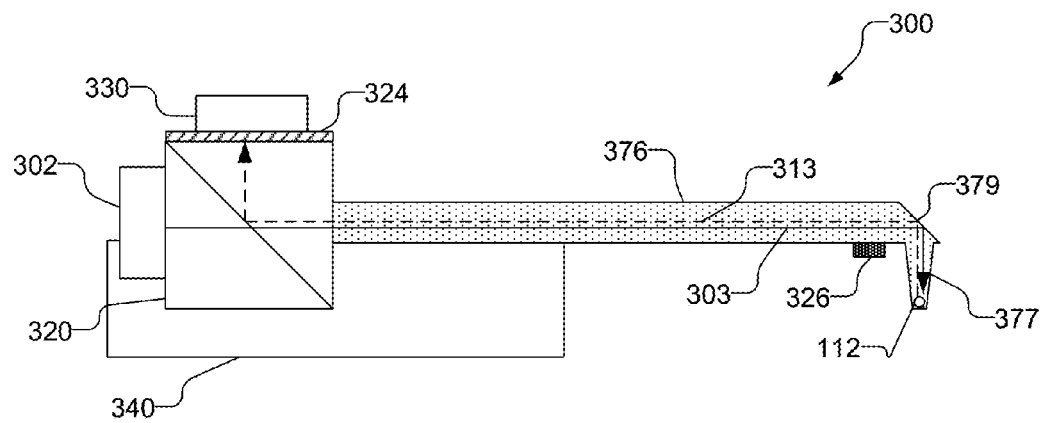
FIG. 29 illustrates a probe arm assembly in which the NV center is positioned at the tip of a probe arm and the detector is attached to the probe arm, e.g., via a beam splitter.

By way of example, FIG. 29 illustrates a probe arm assembly 300 in which the NV center 112 is positioned at the tip of a probe arm 376, similar to the arm 176 discussed in reference to FIGS. 10 and 25. As illustrated, the arm 376 and the tip 377 are produced from a crystal film, such as a diamond film. The NV center 112 is produced to be in the tip 377, as illustrated in FIG. 29. Thus, the arm is a crystal arm with the crystal probe tip at one end with the at least one nitrogen vacancy center in the crystal tip. A beam splitter 320 is connected to the arm 376 and a light source 302 to produce the excitation illumination 303 and a detector 330 for the photoluminescence 313 produced by the NV center 112 are connected to the beam splitter 320. The beam splitter 302 may be is composed of e.g. two micro prisms. The beam splitter 302 may be a dichroic beam splitter, e.g., including optical coatings so that light emitted from the light source 302, e.g., having a wavelength shorter than 600 nm, is transmitted into the probe arm 376 and photoluminescence 313 produced by the NV center 112, e.g., having a wavelength greater than 600 nm, is reflected to the detector 330. Advantageously, the beam splitter 320 and arm 376 may be directly connected, i.e., with no intervening focusing optics disposed between the beam splitter 320 and the arm 376. Moreover, the light source 302 and detector 330 may be connected to the beam splitter 320 so that no intervening focusing optics need be disposed between the light source 302 and the beam splitter 320 and/or the detector 330 and the beam splitter 320. Thus, the excitation illumination from the light source 302 is introduced into an end of the crystal arm 376 that is opposite the end of the crystal arm 376 with the probe tip 377.

Figure 30:
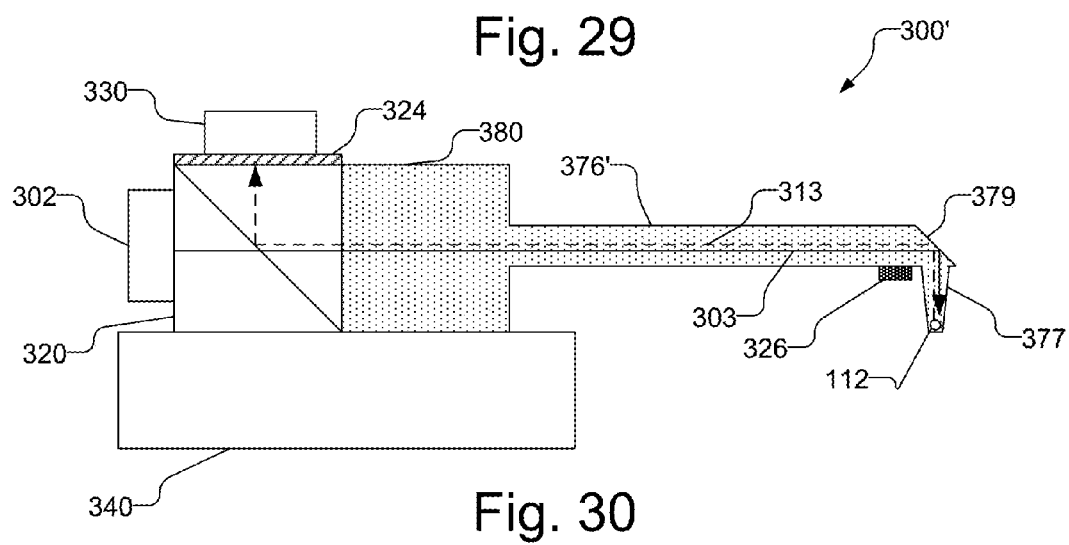
FIG. 30 illustrates another embodiment of a probe arm assembly with an enlarged end of the probe arm.

FIG. 30 illustrates another embodiment of a probe arm assembly 300', that is similar to probe arm assembly 300, like designated elements being the same. The arm assembly 300' of FIG. 30, however, includes an arm 376' that includes an enlarged end 380 that is coupled to the beam splitter 320. The enlarged end 380 enables a greater surface area of the arm 376' to be coupled to the beam splitter 320 thereby a larger interface through which excitation illumination 303 and photoluminescence 313 may be coupled into and out of the arm 376'.

The arm 376 may be produced using a diamond film with NV centers implanted to a desired depth. Lithography, such as electron-beam lithography, may be used to define in a SiO$_2$ mask the probe tip 377 and the enlarged end 380, if used. The diamond film may be etched, e.g., using reactive ion etching (RIE) to define the probe tip 377 and enlarged end 380 if used. Another mask deposition, lithography, and etch process may be used to define the opposite side of the arm 376 including the surface to be mounted to the holder plate 340 and the enlarged end 380, if used. The bevel 397 on the probe arm 376 may be produced, e.g., through isotropic wet-etching with a sacrificial layer, mechanical polishing, anisotropic wet-etching, or focused ion-beam etching. The arm 376 may be cut through the diamond film, e.g., using an etching process. With a sparse implantation of NV centers in the initial diamond film, the resulting probe tip 377 may have only a limited number of NV centers 112. Post processing testing of the probe tip 377 for photoluminescence may be used to ensure the presence and number of NV centers in the probe tip 377.

The light source 302 for either arm assembly 300 or arm assembly 300', collectively referred to herein as arm assembly 300, may be, e.g., a laser diode or LED chip that is mounted to the beam splitter 320. If desired, the light source 302 may include a fiber optic or a light pipe that connects a light emitter, such as a laser or LED, to the beam splitter 320. As discussed previously, the light source 302 may excite the NV center with a continuous (CW) or pulsed excitation illumination, with one or more wavelengths in a range of 460 nm to 580 nm, and which may be, e.g., 532 nm. With pulsed excitation illumination, the pulse width may be, e.g., approximately 800 ps with a 4-MHz repetition rate. The light source 302 may have a power density of, e.g., 40 kW/cm$^2$, to polarize the NV center by pumping it between the ground and the excited levels.

The detector 330 may be e.g., a non-imaging photodetector, such as a silicon avalanche photodiode operating in the single photon regime, i.e., using photon counting, which detects the optical intensity at a single spot. If desired, a CCD or CMOS array may be used, but because the photoluminescence is not being imaged, a CCD or CMOS array is unnecessary. The use of a camera, e.g., using a CCD or CMOS array to provide an overview of the sample during testing, however, may be desirable. As illustrated, a spectral filter 324, such as a dichroic film, may be positioned between the detector 330 and the beam splitter 320. The spectral filter 324 may be an integral part of the beam splitter 320, e.g., an optical coating. The spectral filter 324 removes any reflected excitation illumination 303 and directs only the photoluminescence 313 to the detector 330. The spectral filter 124, thus, may be a long-pass filter with a wavelength cut-off at, e.g., 580 nm, to filter out any remaining pump light. Thus, the detector 330 is physical connected to the beam splitter 320, either directly or with a spectral filter 324 disposed between the detector 330 and the beam splitter 320, with no intervening focusing optics disposed between the beam splitter 320 and the detector 330. The filter 324 may be an integral part of the beam splitter 320, The beam splitter 320 may be, e.g., a micro-prism or a combination of two micro-prisms, that passes the excitation illumination 303 from the light source 302 to the arm 376 and reflects the returning photoluminescence 313 towards the detector 330. If desired, the beam splitter 320 may be configured to reflect the excitation illumination 303 from the light source 302 and transmit the returning photoluminescence 313 to the detector 330. If desired, the beam splitter 320 may be a dichroic beam splitter which may eliminate the need for the spectral filter 324 before the detector 330.

Figure 31:
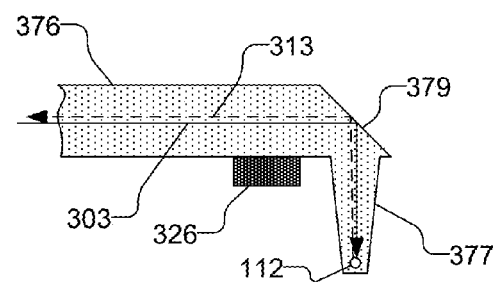
FIG. 31 illustrates a closer view of the tip of the probe arm of the probe arm assembly showing the probe arm acting as a optical waveguide by means of total internal reflection.

As illustrated in FIG. 29, as shown more closely in FIG. 31, arm 376 acts as an optical waveguide by means of total internal reflection. The end 379 of the arm 376 may be beveled to direct the excitation illumination 303 into the tip 377 and to direct the photoluminescence 313 from the NV center 112 into the length of the arm 376. Thus, the excitation illumination 303 from the light source 302 is introduced into the arm 376 via the beam splitter 320, without focusing optics, is guided along the length of the arm 376 via total internal reflection and the arm 376 is configured to reflect the light, e.g., 90°, into the tip 377 to the NV center 112. The arm 376 is configured to reflect photoluminescence 313 from the NV center 112 in the tip 377, e.g., 90°, out of the tip 377 into the arm 376, and the photoluminescence 313 is guided along the length of the arm 376 via total internal reflection until it is received by detector 330, via the beam splitter 320, without focusing optics.

Figure 32:
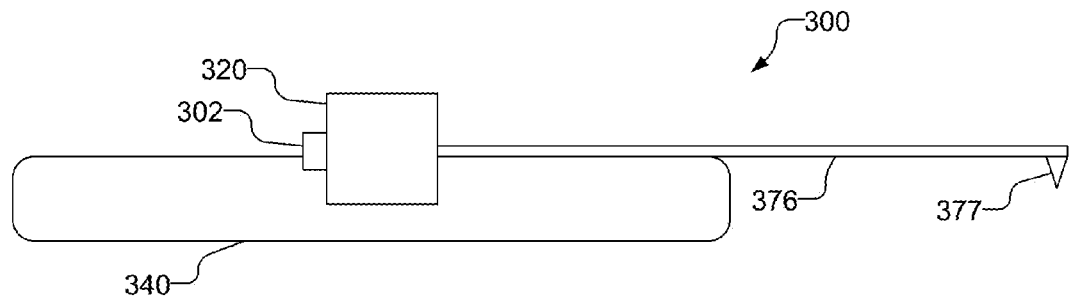
FIGS. 32 and 33, by way of example, illustrate a side view and a top view of the probe arm with a beam splitter mounted on a holder plate.
Figure 33:
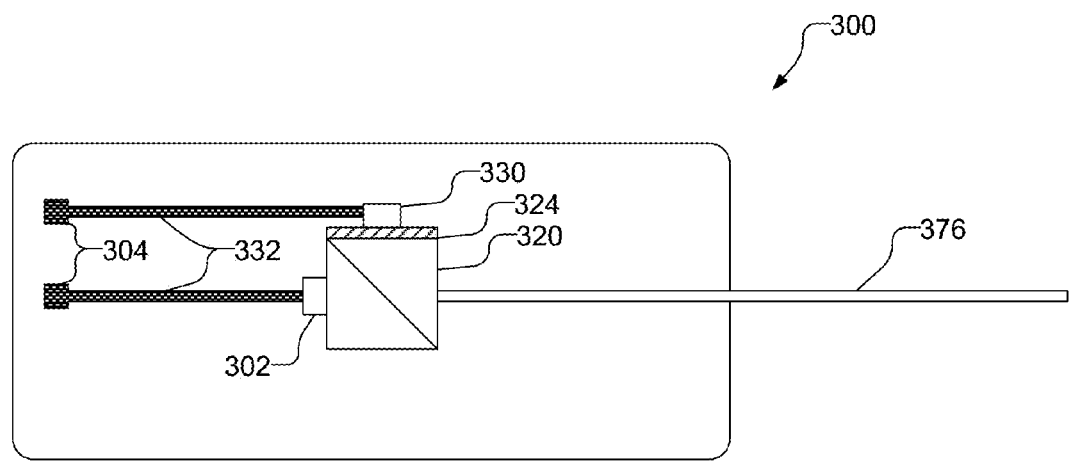

The arm 376 with beam splitter 320 may be mounted on a holder plate 340, which is mounted to the AFM during operation. For example, the arm 376 and beam splitter 320 may be glued to the holder plate 340. For example, the arm 376 may be glued onto the holder plate 340 referenced to an edge on the holder plate 340 or placed in a trench in the holder plate 340. FIGS. 32 and 33, by way of example, illustrate a side view and a top view of the arm 376 with beam splitter 320 mounted on the holder plate 340. The light source 302 and detector 330 may also be mounted on the holder plate 340 if desired and the holder plate 340 may include conductive pads and leads 304 and 332 for the desired electrical connections. Alternatively, one or both the light source 302 and detector 330 may be mounted on the beam splitter 320, which is then mounted on the holder plate 340. For example, FIG. 33 illustrates the detector 330 coupled to the side of the beam splitter 230, along with spectral filter 324, and thus, detector 330 may be mounted to the holder plate 340. FIG. 29, on the other hand, illustrates the detector 330 coupled to the top of the beam splitter 230, and thus, the detector 330 may be mounted to the beam splitter 230, via intervening spectral filter 324.

Figure 34:
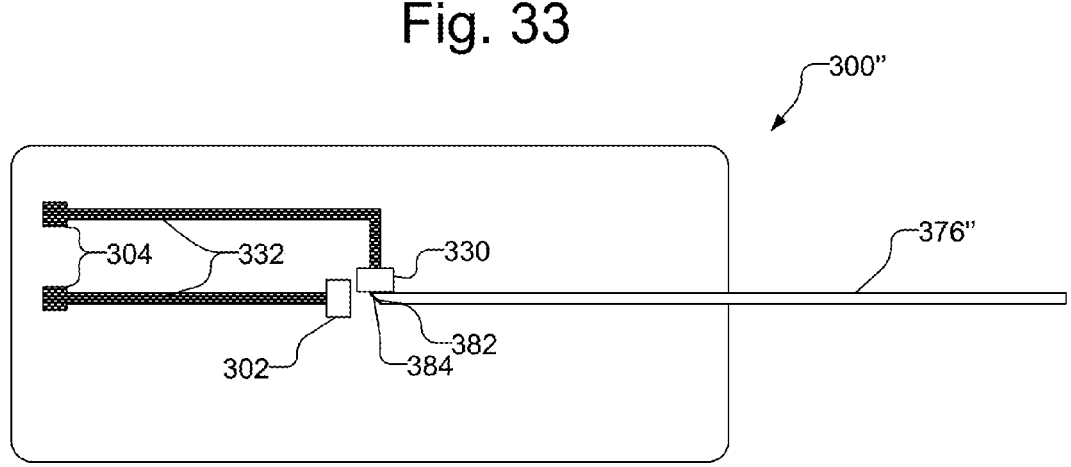
FIG. 34 illustrates a top view of another embodiment of a probe arm assembly with a probe arm connected directly to the detector.

FIG. 34 illustrates another embodiment of an arm assembly 300" that is similar to arm assembly 300, e.g., illustrated in FIG. 33, except that a separate beam splitter 320 is not used with arm assembly 300". As illustrated, the end 382 of the probe arm 376" that is nearest the light source 302 and detector 330 may be beveled, to reflect photoluminescence light to the detector 330. It will be understood that the photoluminescence light is reflected by the beveled portion of the end 382 and is extracted through the side of the probe arm 376" at the end 382, and therefore is referred to herein as being extracted through the end 382. The detector 330 is in direct contact with the side of the probe arm 376" at the end 382 to receive the photoluminescence light that is reflected by the beveled portion of the end 382. A dichroic filter 384 may be deposited on the beveled portion of the end 382 to assist in the reflection of the photoluminescence light but allowing the excitation illumination from light source 302 to enter the probe arm 376". The light source 302 may be separated from the probe arm 376", e.g., by approximately half the width of the detector 330. The apertures of the light source 302 and the detector 330 are centered on the beveled portion of the end 382.

Figure 35:
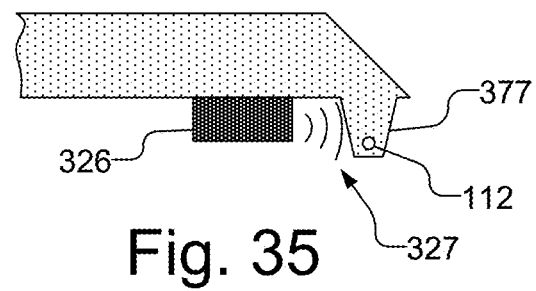
FIG. 35 illustrates a closer view of the tip of the probe arm of the probe arm assembly with an RF antenna.

The arm assembly 300 may be used in the same manner as arm 176 discussed in reference to FIG. 10 to characterize magnetic recording heads. If desired, an RF antenna 326 may be located on the arm 376 to provide an excitation field to the NV center 112. The RF antenna 326 may produce a desired excitation field as discussed above. The RF antenna 326 may be configured, e.g., by positioning and orientation, to produce the desired excitation field that is incident on the NV center 112 but will have little impact on the recording head being tested. For example, with the RF antenna 326 being located close to the NV center 112, a reduced RF excitation field may be used. Moreover, as illustrated in FIG. 35, the RF antenna 326 may be oriented and configured to focus the excitation field 327 on the tip 377 with the NV center 112, and accordingly, little or no excitation field will be directly incident on the recording head. With the presence of the RF antenna 326, the holder plate 340 may include conductive pads and leads for the desired electrical connections. If desired, however, the RF antenna 326 may be separate from the arm 376, e.g., as illustrated in FIG. 10. Thus, the arm 376 may be scanned over the recording head 114 (as illustrated in FIG. 10) in two dimensions and the photoluminescence 113 from the NV center(s) 112 is collected. It should be understood that scanning is performed by producing relative movement between the arm 376 and the sample, e.g., the arm 376 may move in two dimensions and the sample held stationary or the sample may move in two dimensions while the arm 376 is held stationary, or both the arm 376 and sample may move. Additionally, the arm 376 and/or sample may move in the vertical dimension to place the tip 377 in contact with or near the sample. Thus, the tip 377 with the NV center(s) 112 may be in contact with or at a controlled distance from the recording head 114. The ODMR may be measured from the NV center(s) 112 at the tip 377 of the arm 376, at varying excitation frequencies of the excitation field and/or varying magnetic fields produced by the recording head 114 as the arm 376 is scanned over the recording head in two dimensions.

Additionally, the arm assembly 300 may be used in the same manner as arm 176 discussed in reference to FIG. 25 to characterize a photon emitter. If the arm assembly 300 is used to characterize a photon emitter, the RF antenna 326 is not needed. Again, the arm 376 may be scanned over the device being tested, e.g., the photon emitter 119 (shown in FIG. 25) in one or two dimensions and the photoluminescence 113 from the NV center(s) 112 is collected, while the tip 377 with the NV center(s) 112 is in contact with or at a controlled distance from the photon emitter 119. It should be understood that scanning is performed by producing relative movement between the arm 376 and the sample, e.g., the arm 376 may move in two dimensions and the sample held stationary or the sample may move in two dimensions while the arm 376 is held stationary, or both the arm 376 and sample may move. Additionally, the arm 376 and/or sample may move in the vertical dimension to place the tip 377 in contact with or near the sample. The light source 302 produces excitation illumination 303 that is directed to the NV center 112 in the tip 377 via the beam splitter 320 and arm 376. In response to the excitation illumination 103, the NV center 112 produces photoluminescence 113 that is directed back through the arm 376 and provided to the detector 330 via the beam splitter 320. As the arm 376 is scanned across the recording head 114, including the photon emitter 119 and ABS, at each measurement position, the intensity of the photoluminescence 113 is measured with and without the near field illumination 115 from the photon emitter 119 to detect the quenching of the intensity of the photoluminescence at each measuring position. With the photoluminescence quenching detected at a plurality of measuring positions, a one dimensional line profile or two-dimensional distribution of the photoluminescence quenching may be determined. With a two-dimensional distribution of the photoluminescence quenching, the line profile through the strongest quenching point may be used to derive the peak power or the width of the near field illumination profile of the photon emitter by analyzing the amount of quenching of the intensity of the photoluminescence, e.g., by fitting to a photoluminescence quenching model, or compared to a library of data, which may be produced using the model or empirically, as discussed above. If desired, the scan may be repeated for different values of the bias current supplied to the light source, or equivalently, different values of the bias current may be supplied to the light source at each position during a single scan of the arm 376.

With the use of arm assembly 300, with the detector 330 connected to arm 376 via beam splitter 320 to receive photoluminescence 313 without focusing optics, the efficiency of light extraction is improved. Accordingly, the signal to noise ratio is improved and fewer NV centers 112 are required with arm assembly 300, thereby improving spatial resolution. Moreover, measuring time may be decreased as loss of the resulting photoluminescence 313 from the NV centers 112 is reduced or eliminated by guiding the photoluminescence 313 to the detector 330.

Figure 36:
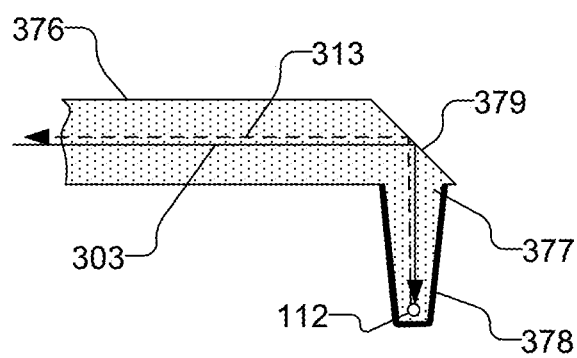
FIG. 36 illustrates a closer view of the tip of the probe arm of the probe arm assembly with an absorption layer.

Additionally, the probe arm 376 may be configured to determine a characteristic of the recording head using measured ODMR based on the heating of the probe tip 377 by a thermal device and near-field transducer in a recording head, such as a HAMR head, as the probe arm 376 is scanned over the sample, as discussed above. For example, a bias signal may be provided to the thermal device, which causes the near-field transducer to heat the probe tip 377. The ODMR may be measured from the NV center(s) 112 at the tip 377 of the arm 376. The increase in temperature caused by the thermal device and near-field transducer affects the electronic state of the NV centers 112, from which a desired characteristic may be determined, as discussed above. Moreover, if desired, as illustrated in FIG. 36, a heat absorption layer 378, similar to the absorption layer 118 discussed above, may be coated on the tip 377 of the probe arm 367, where the thermal device and near-field transducer heat the absorption layer 378 as the probe arm 376 is scanned over the sample.

Although the present invention is illustrated in connection with specific embodiments for instructional purposes, the present invention is not limited thereto. Various adaptations and modifications may be made without departing from the scope of the invention. Therefore, the spirit and scope of the appended claims should not be limited to the foregoing description.

What is claimed is:

1. A method comprising:
   providing a bias signal to a recording head that includes a write pole to produce a magnetic field from the recording head;
   scanning a probe having a probe tip comprising at least one nitrogen vacancy center through the magnetic field produced by the recording head;
   providing an excitation radio frequency (RF) field to the at least one nitrogen vacancy center;
   producing excitation illumination that is incident on the at least one nitrogen vacancy center;
   measuring Optically Detected Spin Resonance (ODMR) by detecting a decrease in a spin dependent photoluminescence in response to the excitation illumination caused by electron spin resonance (ESR) of the at least one nitrogen vacancy center; and
   determining a characteristic of the recording head using the ODMR.

2. The method of claim 1, wherein the probe tip comprises a crystal particle and the at least one nitrogen vacancy center is in the crystal particle, further comprising:
   focusing the excitation illumination on the crystal particle; and
   receiving the spin dependent photoluminescence from the at least one nitrogen vacancy center with a microscope.

3. The method of claim 1, wherein the probe comprises a crystal arm and the probe tip is at a first end of the crystal arm and the at least one nitrogen vacancy center is in the probe tip.

4. The method of claim 3, wherein producing the excitation illumination that is incident on the at least one nitrogen vacancy center comprises introducing the excitation illumination at a second end of the crystal arm that is opposite the first end of the crystal arm, wherein the excitation illumination is guided via total internal reflection through the crystal arm and is reflected into the probe tip.

5. The method of claim 4, wherein introducing the excitation illumination at the second end of the crystal arm is performed without focusing the excitation illumination.

6. The method of claim 4, wherein introducing the excitation illumination at the second end of the crystal arm comprises one of transmitting or reflecting the excitation illumination into the crystal area by a beam splitter that is directly connected to the second end of the crystal arm.

7. The method of claim 6, wherein measuring the ODMR by detecting the decrease in the spin dependent photoluminescence in response to the excitation illumination caused by ESR of the at least one nitrogen vacancy center comprises detecting photoluminescence from the at least one nitrogen vacancy center with a detector that is physical connected to the beam splitter either directly or with a spectral filter disposed between the detector and the beam splitter.

8. The method of claim 4, wherein measuring the ODMR by detecting the decrease in the spin dependent photoluminescence in response to the excitation illumination caused by ESR of the at least one nitrogen vacancy center comprises detecting photoluminescence produced by the at least one nitrogen vacancy center in the probe tip and that is reflected into the crystal arm and extracted through the second end of the crystal arm.

9. The method of claim 8, wherein the photoluminescence extracted through the second end of the crystal arm is detected without focusing the photoluminescence.

10. The method of claim 8, wherein the photoluminescence extracted through the second end of the crystal arm is reflected by the second end of the crystal arm to a detector, and wherein introducing the excitation illumination at the second end of the crystal arm comprises transmitting the excitation illumination into the crystal arm through the second end of the crystal arm.

11. The method of claim 3, wherein the excitation RF field is produced by a radio frequency antenna on the crystal arm.

12. The method of claim 1, wherein the ODMR is measured at varying excitation frequencies of the excitation RF field.

13. The method of claim 1, further comprising providing a plurality of bias signals with different levels to the recording head.

14. The method of claim 1, wherein the recording head further comprises a thermal device and a near-field transducer, the method further comprising:
   providing a second bias signal to the thermal device to heat the probe tip using the near-field transducer; and
   determining a second characteristic of the recording head using measured ODMR based on heating of the probe tip by the thermal device and the near-field transducer.

15. The method of claim 14, wherein the probe tip is coated with a heat absorption layer.

16. The method of claim 14, wherein the second characteristic of the recording head is a near-field power of the near-field transducer.

17. The method of claim 14, wherein the second characteristic of the recording head is a spatial extent of the near-field transducer.

18. The method of claim 14, further comprising providing a plurality of bias signals with different levels to the thermal device and wherein the second characteristic of the recording head is a function of the heat produced at different levels of bias signals.

19. The method of claim 14, wherein the bias signal provided to the recording head and the second bias signal provided to the thermal device are provided sequentially or serially.

20. An apparatus comprising:
   a biasing source configured to provide a bias signal;
   a probe card coupled to the biasing source and configured to be connected to a recording head that includes a write pole to provide the bias signal to the recording head that causes the recording head to produce a magnetic field;
   a probe having a probe tip comprising at least one nitrogen vacancy center, the probe configured to be scanned through the magnetic field produced by the recording head;
   a light source that produces excitation illumination that is incident on the at least one nitrogen vacancy center;
   a radio frequency antenna that provides an excitation field to the at least one nitrogen vacancy center;
   a detector configured to detect photoluminescence produced by the at least one nitrogen vacancy center in the probe tip;
   a processor coupled to the detector and configured to measure Optically Detected Spin Resonance (ODMR) by detecting a decrease in a spin dependent photoluminescence in response to the excitation illumination caused by electron spin resonance (ESR) of the at least one nitrogen vacancy center; and determine a characteristic of the recording head using the ODMR.

21. The apparatus of claim 20, wherein the probe tip comprises a crystal particle and the at least one nitrogen vacancy center is in the crystal particle, further comprising:
   at least one lens configured to focus the excitation illumination on the probe tip and to project photoluminescence produced by the at least one nitrogen vacancy center on the detector.

22. The apparatus of claim 20, wherein the probe comprises a crystal arm and the probe tip is at a first end of the crystal arm and the at least one nitrogen vacancy center is in the probe tip.

23. The apparatus of claim 22, wherein the excitation illumination from the light source is introduced into a second end of the crystal arm that is opposite the first end of the crystal arm, wherein the excitation illumination is guided via total internal reflection through the crystal arm, and, wherein the crystal arm is configured to reflect the excitation illumination into the probe tip.

24. The apparatus of claim 23, wherein the excitation illumination from the light source is introduced into the second end of the crystal arm without focusing optics to focus the excitation illumination.

25. The apparatus of claim 23, further comprising a beam splitter that is directly connected to the second end of the crystal arm, wherein the beam splitter transmits or reflects the excitation illumination from the light source into the crystal arm.

26. The apparatus of claim 25, wherein the detector is physical connected to the beam splitter either directly or with a spectral filter disposed between the detector and the beam splitter.

27. The apparatus of claim 23, wherein the crystal arm is configured to reflect the photoluminescence produced by the at least one nitrogen vacancy center in the probe tip into the crystal arm and the photoluminescence is guided via total internal reflection through the crystal arm and is extracted through the second end of the crystal arm.

28. The apparatus of claim 27, wherein the photoluminescence extracted through the second end of the crystal arm is detected by the detector without intervening focusing optics.

29. The apparatus of claim 27, wherein the second end of the crystal arm is configured to reflect the photoluminescence to the detector, and wherein the excitation illumination from the light source is introduced into the crystal arm by transmitting the excitation illumination through the second end of the crystal arm.

30. The apparatus of claim 22, wherein the radio frequency antenna is on the crystal arm.

31. The apparatus of claim 20, wherein the ODMR is measured at varying excitation frequencies of the excitation field.

32. The apparatus of claim 20, further comprising providing a plurality of bias signals with different levels to the recording head.

33. The apparatus of claim 20, wherein the probe is scanned over a write pole of the recording head and wherein the determined characteristic of the recording head is magnetic field values.

34. The apparatus of claim 20, wherein the recording head further comprises a thermal device and a near-field transducer, the apparatus further comprising:
- a second biasing source configured to provide a second bias signal to the thermal device to heat the probe tip using the near-field transducer;
- wherein the processor is further configured to determine a second characteristic of the recording head using measured ODMR based on heating of the probe tip by the thermal device and the near-field transducer.

35. The apparatus of claim 34, wherein the probe tip is coated with a heat absorption layer.

36. The apparatus of claim 34, wherein the second characteristic of the recording head is a near-field power of the near-field transducer.

37. The apparatus of claim 34, wherein the second characteristic of the recording head is a spatial extent of the near-field transducer.

38. The apparatus of claim 34, wherein the second biasing source provides a plurality of bias signals with different levels to the thermal device and wherein the second characteristic of the recording head is a function of the heat produced at different levels of bias signals.

39. The apparatus of claim 34, wherein the bias signal provided to the recording head and the second bias signal provided to the thermal device are provided sequentially or serially.

\* \* \* \* \*

UNITED STATES PATENT AND TRADEMARK OFFICE
CERTIFICATE OF CORRECTION

PATENT NO. : 9,779,769 B2  
APPLICATION NO. : 14/952852  
DATED : October 3, 2017  
INVENTOR(S) : Juergen Heidmann Page 1 of 1

It is certified that error appears in the above-identified patent and that said Letters Patent is hereby corrected as shown below:

In the Claims

In Column 32, Line 58, in Claim 6, that portion of the claim reading "illumination into the crystal area by a beam splitter" should read -- illumination into the crystal arm by a beam splitter --.

Signed and Sealed this  
Thirteenth Day of November, 2018

Andrei Iancu  
*Director of the United States Patent and Trademark Office*